(12) United States Patent
Niwa et al.

(10) Patent No.: US 7,343,026 B2
(45) Date of Patent: Mar. 11, 2008

(54) OPERATION RECOGNITION SYSTEM ENABLING OPERATOR TO GIVE INSTRUCTION WITHOUT DEVICE OPERATION

(75) Inventors: Kenichi Niwa, Tochigi-ken (JP); Kei Sato, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 731 days.

(21) Appl. No.: 10/784,164

(22) Filed: Feb. 24, 2004

(65) Prior Publication Data

US 2004/0242988 A1 Dec. 2, 2004

(30) Foreign Application Priority Data

Feb. 24, 2003 (JP) ............................. 2003-045554

(51) Int. Cl.
*G06K 9/00* (2006.01)
(52) U.S. Cl. ................... 382/103; 382/128; 715/757
(58) Field of Classification Search ............... 382/103, 382/106, 107, 117, 118, 154, 168, 181, 203, 382/232, 274, 276, 285, 291, 305, 318, 100, 382/128, 129, 130, 131, 132, 133, 189, 295, 382/256; 715/862, 757; 345/427, 419, 7; 348/419, 419.1; 433/24; 378/20, 21
See application file for complete search history.

(56) References Cited

U.S. PATENT DOCUMENTS

| 6,201,516 | B1 * | 3/2001 | Tanide et al. ................... 345/7 |
| 6,204,852 | B1 * | 3/2001 | Kumar et al. ................ 345/419 |
| 6,385,331 | B2 * | 5/2002 | Harakawa et al. .......... 382/106 |
| 6,407,762 | B2 * | 6/2002 | Leavy ......................... 715/862 |
| 6,842,175 | B1 * | 1/2005 | Schmalstieg et al. ....... 345/427 |
| 7,007,236 | B2 * | 2/2006 | Dempski et al. ............ 715/757 |
| 7,029,275 | B2 * | 4/2006 | Rubbert et al. ............... 433/24 |
| 7,161,616 | B1 * | 1/2007 | Okamoto et al. ........... 348/148 |

FOREIGN PATENT DOCUMENTS

JP       2000-222098       8/2000

\* cited by examiner

*Primary Examiner*—Seyed Azarian
(74) *Attorney, Agent, or Firm*—Oblon, Spivak, McClelland, Maier & Neustadt, P.C.

(57) ABSTRACT

An operation recognition system including an object to be operated, at least one camera, a processor, and a controller. At least one camera is configured to acquire image data of an operator in a predetermined period of time, and a processor is configured to perform recognition processing on the acquired image data. Upon processing the image data, the processor is configured to define a virtual plane in between the object to be operated and the operator. The processor is configured to then perform a process to determine if a predetermined part of the operator penetrates the virtual plane based on the recognition processing. Based on this determination, the controller is configured to control the object to be operated.

34 Claims, 14 Drawing Sheets

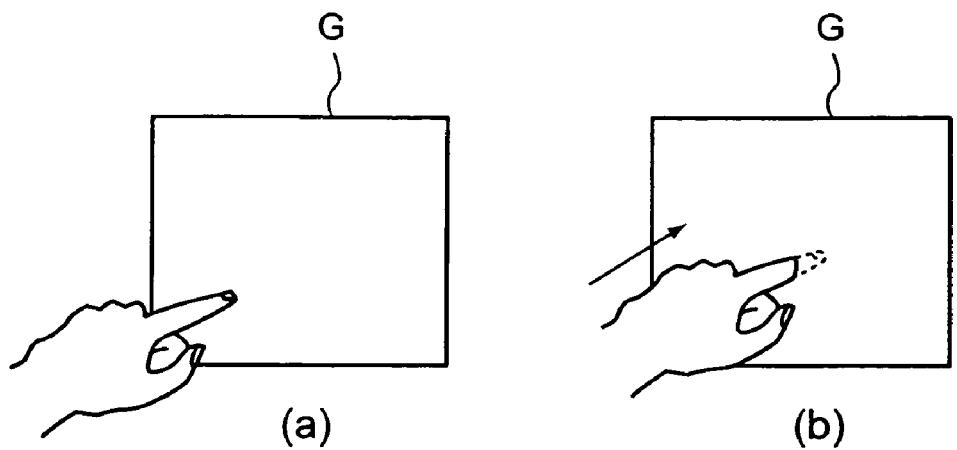
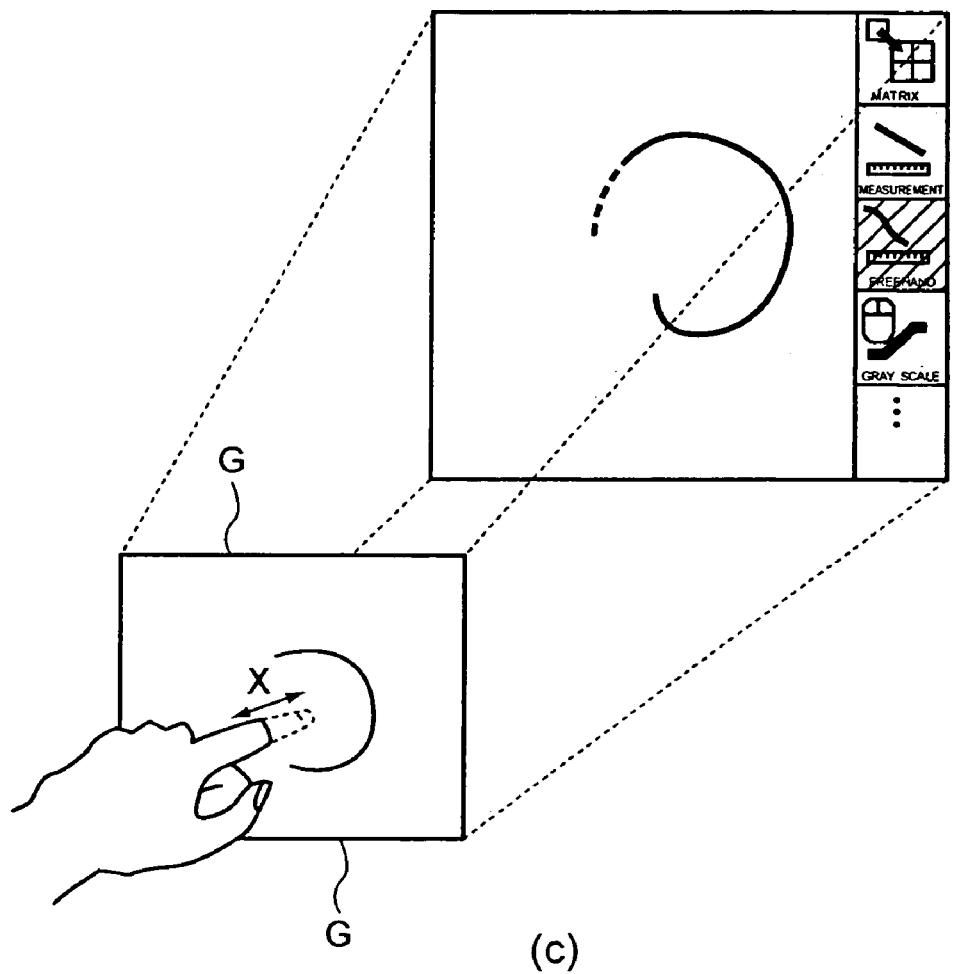
FIG. 8

OPERATION RECOGNITION SYSTEM ENABLING OPERATOR TO GIVE INSTRUCTION WITHOUT DEVICE OPERATION

CROSS-REFERENCE TO RELATED APPLICATION

This application is based upon and claims the benefit of priority from prior Japanese Patent Application No. P2003-45554, filed on Feb. 24, 2003, the entire contents of which are incorporated herein by reference.

BACKGROUND OF THE INVENTION

1. Field of the Invention

The present invention relates to an operation recognition system which recognizes a user's operation without a device and controls an object based on the recognition.

2. Discussion of the Background

In the medical field, an image display apparatus is used to support image interpretation, medical examinations, and explanation to patients, for example, through a graphical user interface (GUI). Such an image display apparatus is known as a workstation or an image viewer and is described, for example, in Japanese Patent Application Publication No. PH5-12352.

In general, the GUI used in the image viewer is typically a keyboard, a mouse, or an operation panel particularly provided as the GUI. The image viewer also includes an image display unit, such as, for example, a display monitor or a projector. An operator of the image viewer such as a doctor operates the keyboard, the mouse, and/or the operation panel so as to select, change, and/or set display conditions of medical images or medical examination reports to be displayed in the display monitor orb the projector. Accordingly, desired medical information is displayed in the display monitor or by the projector. Regarding the displayed medical information, the operator can also adjust its size, its alignment, its image quality, its gray scale, and soon. In addition, the operator may add necessary information to the displayed medical information as annotation information.

Medical images are usually acquired by medical imaging apparatuses such as a digital radiography apparatus, an X-ray computed tomography apparatus, a magnetic resonance imaging apparatus, and the like. The acquired images are stored in an image server. Medical examination reports are usually prepared by report clients in a report system or by the medical imaging apparatuses. The prepared reports are stored in a report server in the report system. The stored images and reports can be retrieved from the image server and the report server to the image viewer, respectively, in accordance with operations by the operator, using the keyboard, the mouse, and/or the operation panel. The image viewer is also used to display the acquired images in image interpretation resulting in the preparation of the medical examination report. The operator observes the images displayed in the image viewer and prepares the medical examination report in the report client.

In the image interpretation or the image reference, the operator needs to operate the keyboard, the mouse, and/or the operation panel so as to display desired images or desired reports. Particularly when it comes to an occasion of a conference, quite a number of operators exist for referring to images or reports. The operators need to hand over the keyboard, the mouse, and/or the operation panel to one another during the conference. Such a handover is inconvenient for the operators and restricts their operations. Further, in case of a surgery or an operative treatment, a doctor is not allowed to touch and operate the keyboard or the like during the surgery or the operative treatment from a hygienic point of view. For example, Japanese Patent Application Publication No. P2000-222098 describes a hand pointing device which recognizes a shape of an operator's hand and is operative in response to the recognition without an input operation by a keyboard and a mouse.

Such a hand pointing device, however, does not enable the operator to perform the following operations which are usually implemented in a conventional image viewer. Such operations include a drag operation and a double click operation through a mouse operation, and a drawing operation in the screen. The drawing operation includes desired drawing of lines, figures, and characters in the screen.

SUMMARY OF THE INVENTION

According to a first aspect of the present invention, there is provided an operation recognition system. The system includes an object to be operated, at least one camera, a processor, and a controller. The at least one camera is configured to acquire image data of an operator. At least the predetermined number of image data is acquired in a predetermined time period. The processor is configured to process the acquired image data so as to recognize the operator. The processor is further configured to define a virtual plane in between the object and the operator and to determine if a predetermined part of the operator penetrates the virtual plane based on the recognition. The controller is configured to control the object based on the determination.

According to a second aspect of the present invention, there is provided an image display apparatus for displaying an image. The apparatus includes a display, a position detector, a virtual plane defining element, a determining element, and a display control element. The display is configured to display the image in a screen. The position detector is configured to detect the position of an operator and the position of an operator's hand. The virtual plane defining element is configured to define a virtual plane in between the screen and the operator based on the position of the operator. The determining element is configured to determine a virtual contact between the virtual plane and the operator's hand based on the position of the operator's hand and a position of the virtual plane. The display control element is configured to control the display of the image based on determination by the determining element.

According to a third aspect of the present invention, there is provided an image display apparatus for displaying an image. The apparatus includes a display, an imaging element, a position detector, a virtual plane defining element, a determining element, and a display control element. The display is configured to display the image in a screen. The imaging element is provided at both sides of the screen and is configured to acquire image data of the operator from different directions. The position detector is configured to detect the position of the operator relative to the screen and the position of an operator's hand based on the acquired image data. The virtual plane defining element is configured to define a virtual plane in between the screen and the operator based on the position of the operator. The determining element is configured to determine a virtual contact manner between the virtual plane and the operator's hand based on the position of the operator's hand and a position of the virtual plane. The display control element is configured to determine an operation item corresponding to the contact manner based on determination by the determining element. The display control element is further configured to control the display of the image according to the operation item.

According to a fourth aspect of the present invention, there is provided a method of controlling an object. The method begins by acquiring image data of an operator. At least the predetermined number of image data is acquired in a predetermined time period. The method continues by processing the acquired image data so as to recognize the operator, and defining a virtual plane in between the object and the operator. The method further continues by determining if a predetermined part of the operator penetrates the virtual plane based on the recognition. The method still further continues by controlling the object based on the determination.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 8 is an illustration showing an example of a freehand drawing according to the first embodiment of the present invention;

DESCRIPTION OF THE PREFERRED EMBODIMENTS

Embodiments of the present invention will be described with reference to the accompanying drawings.

First Embodiment

<Medical Image Display System>

Figure 1:
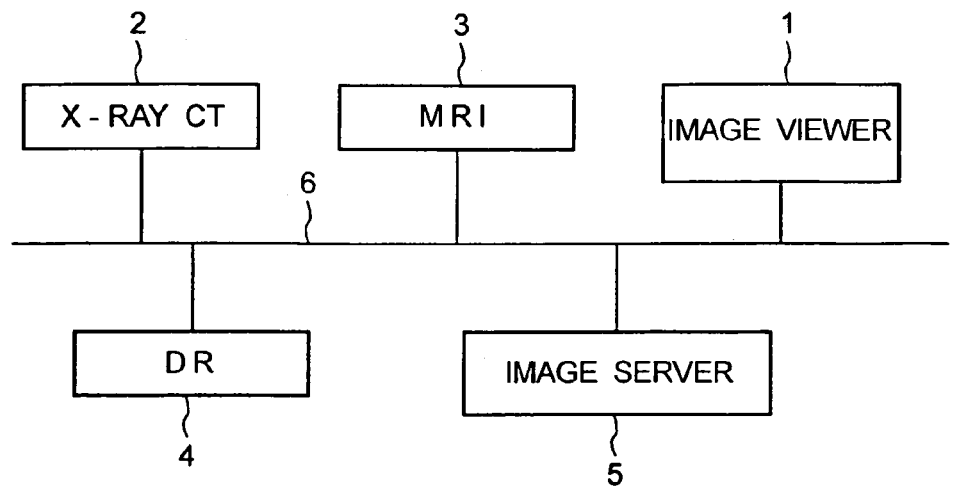
FIG. 1 is a block diagram showing an exemplary medical image display system according to a first embodiment of the present invention.

FIG. 1 is a block diagram showing an exemplary medical image display system according to a first embodiment of the present invention. As shown in FIG. 1, the medical image display system includes an image viewer 1, an X-ray computed tomography apparatus 2, a magnetic resonance imaging apparatus 3, a digital radiography apparatus 4, and an image server 5.

The image viewer 1 includes a display for displaying images and an input unit for inputting information or instructions. The display may also be used to display medical examination reports based on medical image interpretations. The input unit includes a keyboard, a mouse, and/or an operation panel. The X-ray computed tomography apparatus 2, the magnetic resonance imaging apparatus 3, and the digital radiography apparatus 4 acquire medical images, respectively. The digital radiography apparatus 4 is used in combination with an X-RAY fluoroscopy (not shown in FIG. 1) and digitally processes X-ray images. The acquired medical images are stored in the image server 5. The image server 5 may also store the medical examination reports. The components shown in FIG. 1 are connected to and communicate with one another through a network such as a local area network (LAN) 6. The medical image display system may further include one or more alternative medical imaging apparatuses such as, for example, an X-ray diagnosis apparatus, an ultrasound diagnosis apparatus, an endoscope, and a nuclear medical diagnosis apparatus. Further, the medical image display system may include a report system. The report system includes a report server and a report client. The report server can be used to store the medical examination reports so that the image server 5 is not required to store the medical examination reports. Similarly, the report client can be used to prepare the medical examination reports. The report client is also used to display the prepared medical examination reports.

When medical image data has been acquired in the X-ray computed tomography apparatus 2, the magnetic resonance imaging apparatus 3, and/or the digital radiography apparatus 4, the acquired medical image data is usually transmitted to and stored in the image server 5. An operator such as a doctor operates the input unit in the image viewer 1 so as to retrieve desired medical image data stored in the image server 5. The retrieved medical image data is displayed in the image viewer 1. The doctor observes and interprets the displayed images and accordingly prepares medical examination reports on the interpreted images. The prepared medical examination reports are stored in the image server 5. Once the medical examination reports are stored in the image server S, the medical examination reports can be retrieved and displayed in the image viewer 1. According to the first embodiment of the present invention, the image viewer 1 includes a virtual operation panel as a second operation panel. The virtual operation panel includes a virtual plane and a virtual keyboard which are defined at predetermined positions in a virtual space, respectively. The virtual operation panel will be described in further detail below.

<Medical Image Display>

Figure 2:
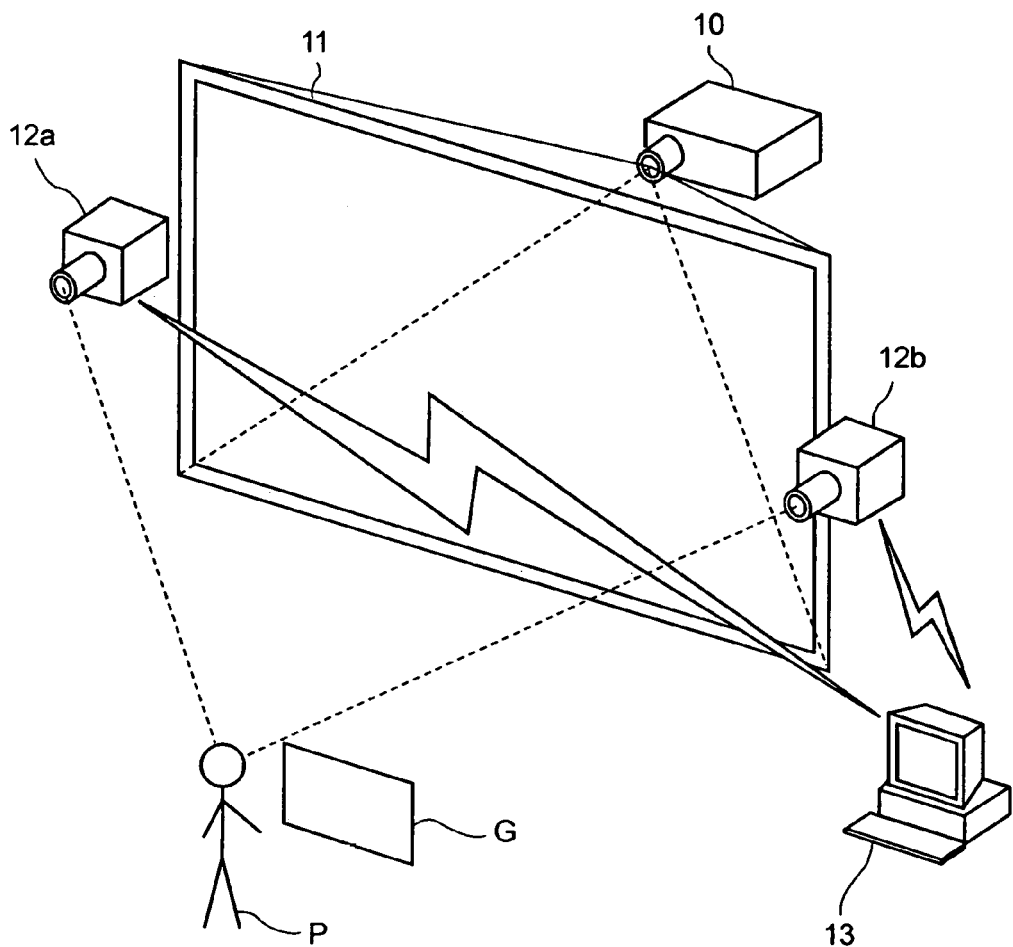
FIG. 2 is an illustration showing an exemplary configuration of an image viewer according to the first embodiment of the present invention.

The image viewer 1 will be described below. According to the first embodiment, explanation of the image viewer 1 may also be applied to the report client although the report client is not described below. FIG. 2 is an illustration showing an exemplary configuration of the image viewer 1 according to the first embodiment of the present invention.

In addition to the components described above, the image viewer 1 further includes a projector 10, a screen 11, video cameras 12a and 12b, and a controller 13. The projector 10 projects a display window to the screen 11. The display window is what is usually displayed in the display described above. Therefore, an operator P can observe images in the screen 11. The video cameras 12a and 12b are provided at both sides of the screen 11. The video cameras 12a and 12b are used to detect positions of operator P's hands, eyes, and any other necessary body part. One of the operator P's eyes is determined as a view point of the operator P. When the operator P opens only one eye, the open eye can be the view point. Otherwise, one of the operator P's eyes is determined as the view point in advance. The one eye (a left eye or a right eye) may be predetermined for every operator P. The controller 13 implements image processing on image data acquired by the video cameras 12a and 12b and calculates a distance between the view point and the screen 11 based on the image data. The controller 13 also defines a virtual plane G within an extension from the view point to each corner of the screen 11 (e.g., see FIG. 4) based on the calculated distance, the view point, and the predetermined size of the screen 11. Since the operator P's motion is imaged by the video cameras 12a and 12b, the controller 13 determines whether the operator P brings his or her fingertip to penetrate the virtual plane G based on the image processing. In response to the penetration, the controller 13 controls the image viewer 1 in accordance with the penetrated part in the virtual plane G. The control of the image viewer 1 is reflected in the display of the screen 11. Instead of the projector 10 and the screen 11, the image viewer 1 may include a cathode ray tube (CRT) monitor, a liquid crystal display (LCD), or any other commercially available display. The projector 10, the video cameras 12a and 12b, and the controller 13 are connected by cables, infrared data communication, or the like.

<Controller>

Figure 3:
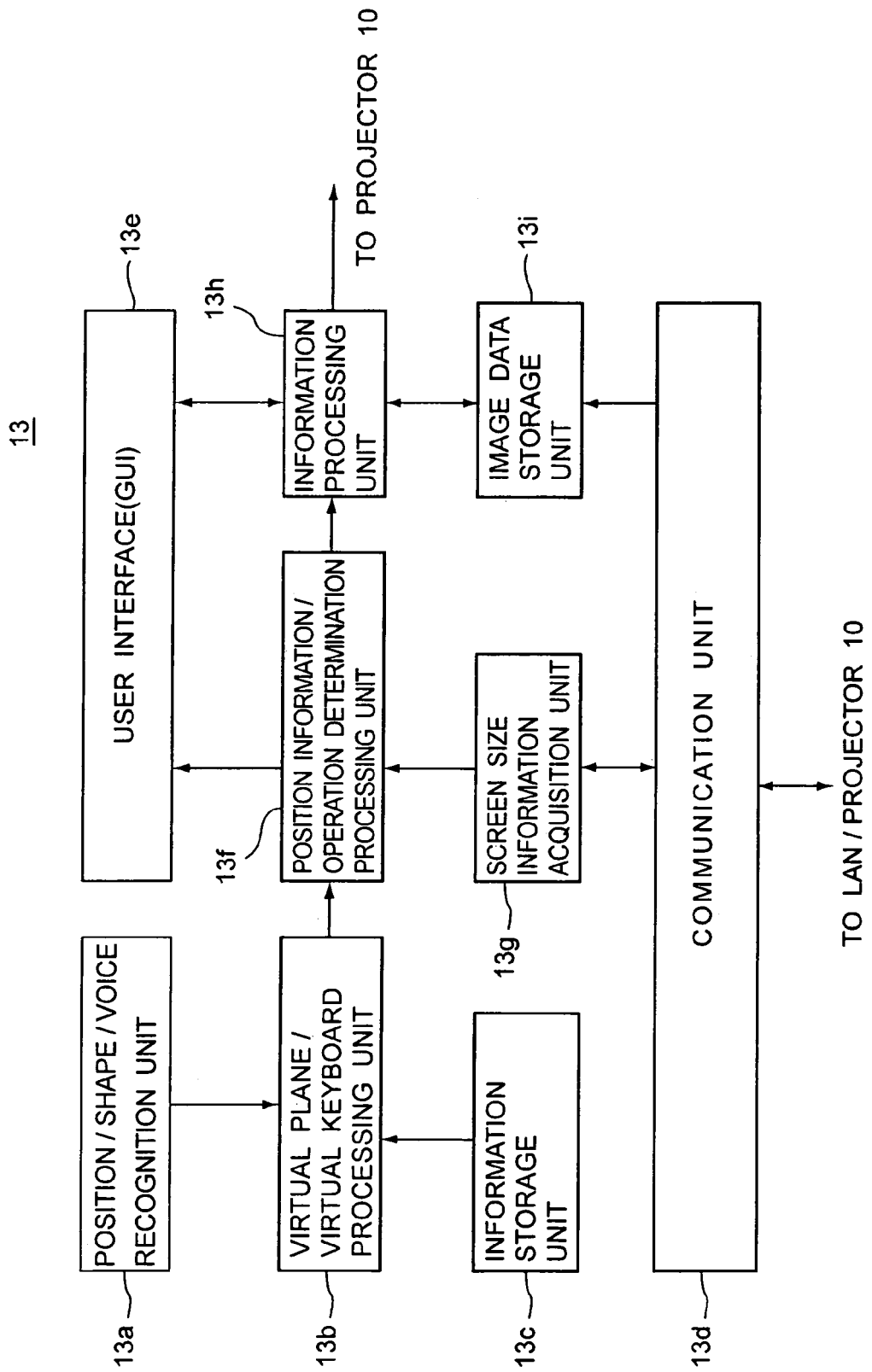
FIG. 3 is a block diagram showing an exemplary configuration of a controller according to the first embodiment of the present invention.

FIG. 3 is a block diagram showing an exemplary configuration of the controller 13 according to the first embodiment of the present invention. As shown in FIG. 3, the controller 13 includes a recognition unit 13a, a first processing unit 13b, a first storage unit 13c, a communication unit 13d, a user interface 13e, a second processing unit 13f, an information acquisition unit 13g, a third processing unit 13h, and a second storage unit 13i.

The recognition unit 13a recognizes a position, a shape, and/or a voice of the operator P. For example, the recognition unit 13a detects a position of the operator P such as, for example, positions of eyes or a position of a head, and three-dimensional positions of hands of the operator P (particularly, fingertip of the operator P). The first processing unit 13b processes the virtual plane G and the virtual keyboard. For example, the first processing unit 13b defines the virtual plane G in between the operator P and the screen 11. The first processing unit 13b further defines the virtual keyboard in a three-dimensional position in the virtual plane G. The first storage unit 13c stores individual information regarding the operator P. The communication unit 13d retrieves image data and/or medical examination reports from the image server 5 through the LAN 6. The communication unit 13d may also be connected to the projector 10. The user interface 13e includes a graphical user interface (GUI) and is used for input operations through the virtual plane G and/or the virtual keyboard. The second processing unit 13f converts three-dimensional position information of the hand(s) of the operator P to two-dimensional coordinates information. The second processing unit 13f also determines a click operation based on the position(s) of the virtual plane G and/or the virtual keyboard and the three-dimensional position information of the hand. The information acquisition unit 13g acquires a size of an image displayed in the screen 11, that is, screen size information. The third processing unit 13h processes operations made through the user interface 13e so as to implement an image display resulting from image processing in accordance with the operations The third processing unit 13h is connected to the projector 10. The second storage unit 13i stores information of image data and medical examination reports to be displayed in the screen 11.

In the above-described configuration of the controller 13, when the operator P enters into a predetermined effective area, the video cameras 12a and 12b acquires a figure of the operator P as image data. The predetermined effective area may be an area corresponding to a field of view of the video cameras 12a and 12b. The recognition unit 13a obtains three-dimensional position information of eye(s) and/or hand(s) of the operator P based on the acquired image data. The obtained three-dimensional position information is transferred to the first processing unit 13b and the second processing unit 13f. Since the video cameras 12a and 12b are provided at positions in a predetermined relationship with the screen 11, the three-dimensional position information of the eye(s) and the hand(s) represents a relative positionnal relationship with the screen 11.

When the image viewer 1 requires an authority for operating the image viewer 1 on the operator P, the operator P may have to show his or her hand in the predetermined effective area. It is also necessary to store a hand shape of every permitted operator P in the first storage unit 13c in advance. The recognition unit 13a recognizes the hand shape of the operator P who wants to operate the image viewer 1. If the recognized hand shape is substantially identical to one of the stored hand shapes, the operator P is authorized to operate the image viewer 1. Accordingly, following operations by the operator P become effective. Such an authority determination may alternatively be made by or may be combined with voice recognition in the recognition unit 13a.

When a plurality of operators P appear in the predetermined effective area, the controller 13 allows only one of the operators P to operate the image viewer 1. In other words, operations by only one operator P are treated as effective operations. In order to determine only one operator P, the image viewer 1 requires the operator P to show his or her hand. The recognition unit 13a recognizes the hand shape based on the acquired image data. For example, a particular shape of the hand may be required for the operator determination. Instead of the hand shape, the operator P may bring his or her hand to the front of his or her face. Such a motion can be recognized by the recognition unit 13a based on the acquired image data. The operator determination may alternatively be or be combined with voice recognition. For example, one operator P who uttered a predetermined word is allowed to operate the image viewer 1. The recognition unit 13a recognizes the predetermined word based on collected speech data resulting from the operator P's utterance. The predetermined word and/or the particular shape of the hand are stored in the recognition unit 13a or in the first storage unit 13c in advance.

Once the operator P is allowed to operate the image viewer 1, the recognition unit 13a obtains three-dimensional position information of eye(s) and hand(s) of the operator P based on the acquired image data. The obtained three-dimensional position information is transferred to the first processing unit 13b and the second processing unit 13f.

The recognition unit 13a further sets a view point. The view point can be set to an opening eye when the operator P opens only one eye. When the operator P opens both eyes, a dominant eye of the operator P can be set as the view point. Information of the dominant eye may be input from the input unit by the operator P. Another way of indicating the dominant eye maybe recognition through acquired image data that the operator P raises one hand on the same side as the dominant eye. Still alternatively, when a hand shape of every permitted operator P is stored in the first storage unit 13c, the dominant eye may be stored in correspondence with the hand shape for every permitted operator P. The storage may be made, for example, in a table form. As additional information, the storage may also include operation authority, that is, the permissible operations that can be performed by each operator P.

The recognition unit 13a implements calculations for obtaining, for example, a height of the view point, a distance between the view point and the screen 11, and a distance between the recognized hand and the screen 11.

The first processing unit 13b defines the virtual plane G at a predetermined position within an extension from the view point to the screen 11 based on the three-dimensional position information of the operator P's eyes. Three-dimensional position information of the virtual plane G is transferred to the second processing unit 13f.

Figure 4:
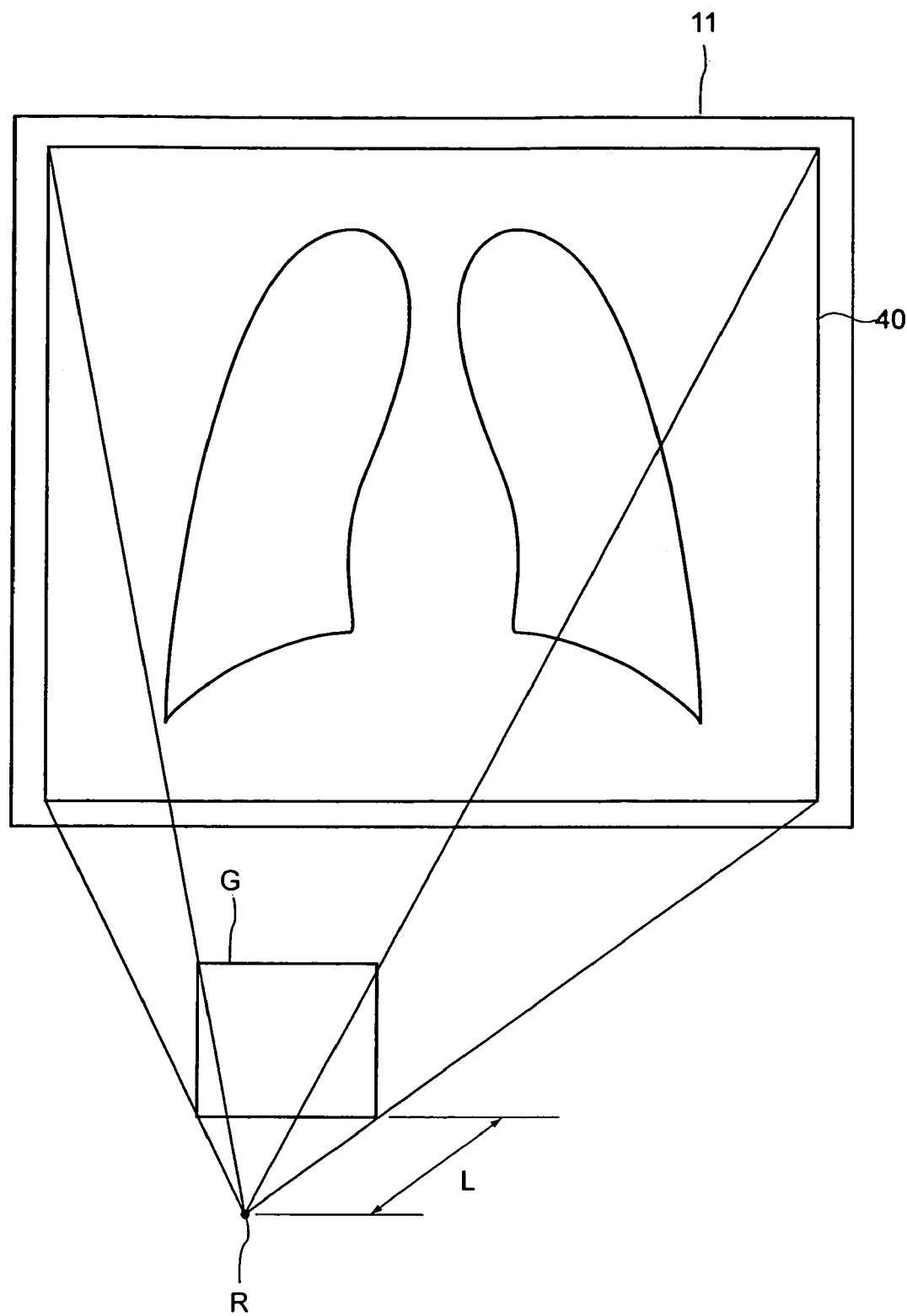
FIG. 4 is an illustration for explaining an example of definition of a virtual plane according to the first embodiment of the present invention.

For the definition of the virtual plane G, the first processing unit 13b determines a position in a distance L of a half length of the operator P's arm from a view point R of the operator P as shown in FIG. 4. The virtual plane G is defined at the position in the distance L from the view point R. The virtual plane G is preferably defined in parallel with the screen 11. For obtaining the arm length of the operator P, for example, predetermined markers are put on a shoulder, an elbow, and a hand of the operator P. The video cameras 12a and 12b acquires image data of the operator P with the markers. The recognition unit 13a implements image processing on the acquired image data and recognizes positions of the markers. By the recognition, the positions of the markers are abstracted. The first processing unit 13b calculates a first distance between the marker on the shoulder and the marker on the elbow based on the abstracted positions. Similarly, the first processing unit 13b calculates a second distance between the marker on the elbow and the marker on the hand based on the abstracted positions. Finally, the first processing unit 13b adds the first distance and the second distance so as to obtain the arm length of the operator P.

Each corner of the virtual plane P is preferably on an extension from the viewpoint R to a corresponding corner of a display window 40 projected to the screen 11. Accordingly, each point in the virtual plane G corresponds to a similar point in the display window 40. The distance L may be variable and changed according to preference of the operator P. An initial distance maybe preset as the distance L by the operator P. The distance L may also be fixed or initially predetermined by the system. The size of the virtual plane G is also not limited to the above case on the extension from the view point R to the screen 11. Further, it is not necessary to define the virtual plane G in parallel with the screen 11.

Figure 5:
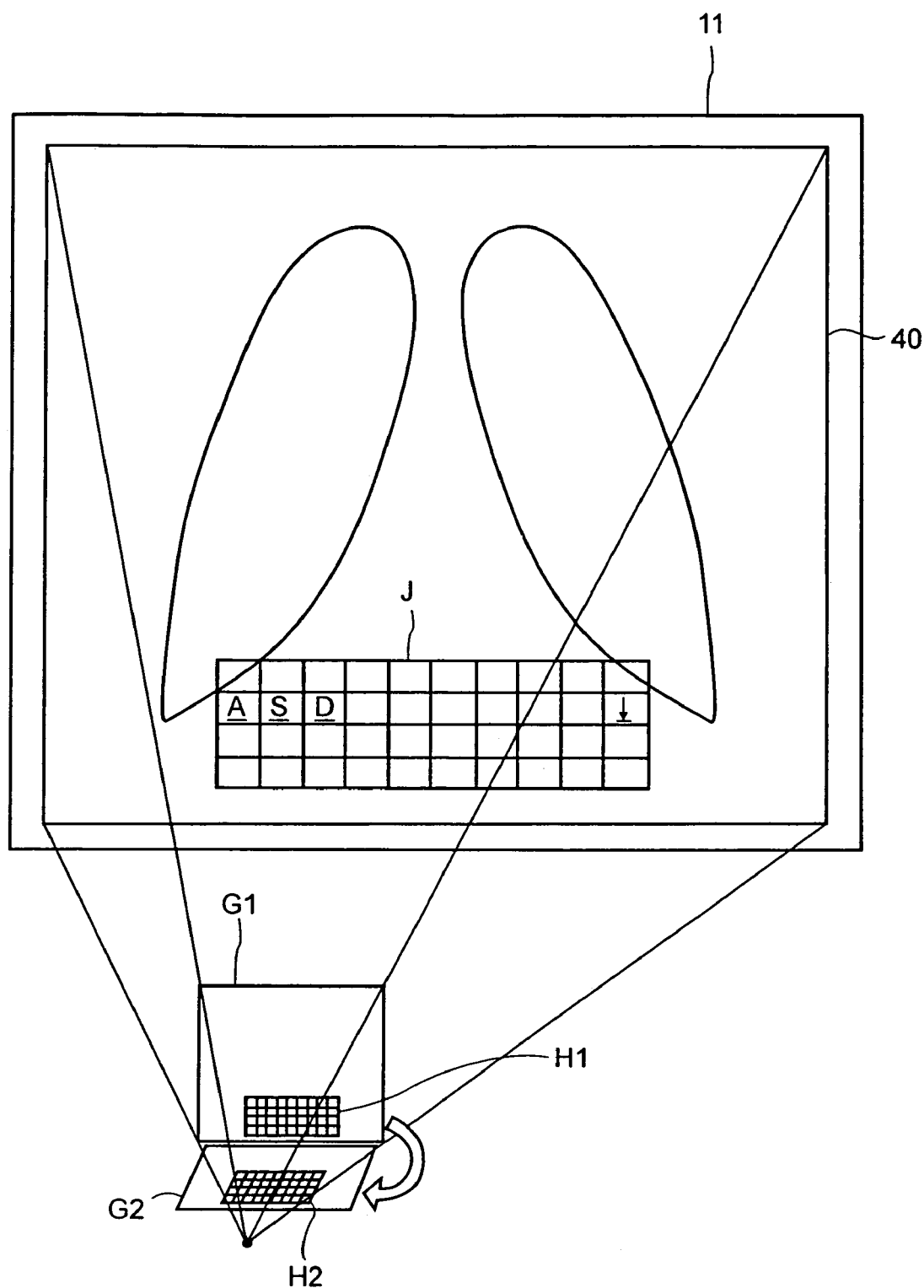
FIG. 5 is an illustration for explaining an example of a virtual keyboard according to the first embodiment of the present invention.

The first processing unit 13b further defines the virtual keyboard at a predetermined position in the virtual plane G. Three-dimensional position information of the virtual keyboard is transferred to the user interface 13e via the second processing unit 13f. The predetermined position where the virtual keyboard is defined may be variable within the virtual plane G. As shown in FIG. 5, when a virtual keyboard H1 is defined in a virtual plane G1, the user interface 13e is operative so as to display a screen keyboard J in the screen 11 as a graphic image. The screen keyboard J corresponds to the virtual keyboard H1. Therefore, operations on the virtual keyboard H1 by the operator P is reflected on the screen keyboard J which enables the operator P to see which key the operator P is pressing. For example, a key in the screen keyboard J corresponding to the key pressed on the virtual keyboard H1 is differentiated from others in color. In case that it is difficult to operate such a virtual keyboard H1, a simplified virtual keyboard may be defined as an alternative. For example, the simplified virtual keyboard may include fewer keys in a larger size so that the operator P can easily press desired keys.

When the operator P feels it troublesome to operate the virtual keyboard H1 within his or her view while the operator P is confirming pressed keys in the screen 11, it may be possible to define an alternative virtual keyboard H2 in another virtual plane G2. The virtual plane G2 is, for example, defined in parallel with a floor where the operator P stands. In this case, however, another video camera is needed on the floor so as to acquire image data, to define another virtual plane G2, and to implement image processing for the operations on the virtual keyboard H2. Even when another virtual plane G2 is defined, the screen keyboard J is displayed in the screen 11 in a manner corresponding to the virtual keyboard H2. Therefore, the operator P can confirm in the screen 11 which key the operator P is pressing.

The information acquisition unit 13g acquires information regarding a size of the display window projected to the screen 11. The size of the display window is determined based on a distance between the screen 11 and the projector 10 and an image expansion scale set in the projector 10. For example, information of the distance between the screen 11 and the projector 10 is stored in the information acquisition unit 13g in advance. Also for example, information of the image expansion scale is available from the projector 10 through the communication unit 13d.

The second processing unit 13f receives the information regarding the size of the display window from the information acquisition unit 13g. The second processing unit 13f also receives the three-dimensional position information of the eye and hand of the operator P from the recognition unit 13a. Based on the received information, the second processing unit 13f calculates corresponding two-dimensional coordinate information in the display window projected to the screen 11. The calculated information is transferred to the user interface 13e. Further, the second processing unit 13f determines whether a (double) click operation is made or not based on the three-dimensional position information such as, for example, the position of the operator P's fingertip and the position of the virtual plane G. The determination result is transferred to the third processing unit h. The click operation will be described below.

The user interface 13e performs processes to display graphic images for input operations. The graphic images include icons, the screen keyboard, and a cursor. The user interface 13e also implements processing regarding the input operations. In more detail, the user interface 13e processes a cursor move based on the two-dimensional coordinate information from the second processing unit 13f. When a click operation is made at a position of an icon in the virtual plane G, the user interface 13e instructs the third processing unit 13h to implement processing or operations defined by or related to the icon. Also when a click operation is made on a key of the virtual keyboard, the user interface 13e determines that a number or a character corresponding to the clicked key has been input by the operator P. The number or character information is transferred to the third processing unit 13h.

The third processing unit 13h executes a software program corresponding to the processing or the operations instructed by the user interface 13e so as to implement the processing or the operations. The third processing unit 13h may obtain other information such as, for example, the coordinate information and the click determination result from the user interface 13e if necessary for the processing or the operations. As a result of the processing in the second processing unit 13f, the user interface 13e, and the third processing unit 13h, the processed or operated result corresponding to the click operation is projected to the screen 11 by the projector 10 and displayed in the screen 11. Image data or the like to be required in the processing or the operation are stored in the second storage unit 13i in advance. When such data are not stored in the second storage unit 13i, such data may be pre-fetched from the image server 5 through the communication unit 13d and stored in the second storage unit 13i.

<Second Processing Unit>

Processing in the second processing unit 13f will be described in detail below. Such processing includes a cursor move, a click operation, a double click operation, and a drag operation, which are made in the virtual plane G. The processing further includes an input operation in the virtual keyboard.

In the image viewer 1, various operation modes are prepared for assisting the operator such as a doctor to interpret medical images. For example, a matrix change mode may be prepared for changing a matrix of image display. When a 2×2 matrix is set, four images are displayed at one time. If the operator P prefers to observe 16 images at one time, the 2×2 matrix is changed to a 4×4 matrix according to the matrix change mode. A distance measurement mode may also be prepared for measuring a distance between desired two points in an image displayed in the display window projected to the screen 11. A freehand mode may further be prepared for drawing a desired line in freehand in an image displayed in the display window projected to the screen 11. A gray scale change mode may still further be prepared for changing a gray scale of an image displayed in the display window projected to the screen 11. Furthermore, a text input mode may be prepared for inputting and displaying numbers, characters, and symbols as annotation in an image displayed in the display window projected to the screen 11. Any other necessary operation mode may be prepared according to the necessity.

As described above, the second processing unit 13f calculates the two-dimensional coordinate information in the display window projected to the screen 11 based on the three-dimensional position information of the eye and hand of the operator P obtained in the recognition unit 13a. In this calculation, coordinates are obtained which are positioned at an intersection where an extension from the position of the operator P's eye (the view point) to the position of the operator P's fingertip intersects with the display window projected to the screen 11. Accordingly, the obtained coordinates correspond to a point where the operator P sees his or her fingertip pointing against the display window.

Here, a parameter S is defined as a time period (second) when the operator P's fingertip is penetrating the virtual plane G. Further, a parameter X is defined as a distance (millimeter) by which the operator P's fingertip penetrates the virtual plane G. The second processing unit 13f includes a timer and a processing section (both are not shown in FIG. 3). The timer is used to measure the time period S. The processing section is used to detect or determine the distance X. The second processing unit 13f will make the following determinations based on the time period S and the distance X.

<<Click Operation>>

A click operation against the virtual plane G is basically recognized by image processing on image data acquired by the video cameras 12a and 12b. Since two video cameras 12a and 12b are used to acquire image data, it is possible to implement three-dimensional image processing. As a result of such image processing, motions of the fingertip can be recognized. The number of video cameras may be more than two.

When only one video camera is used to acquire image data, the click operation is recognized by the size difference of the fingertip between before and after the click operation. Alternatively, the recognition may be accomplished by an automatic focus feature which is well known in the field of camera. Another way of performing the recognition is to use a distance measurement sensor which is also commercially available.

The idea of such recognition of the click operation is also applied to the double click operation and the drag operation.

When the distance X is more than a predetermined distance and the time period S is within a predetermined time period, the second processing unit 13f determines that a click operation has been performed by the operator P. For example, the determination conditions (or thresholds) may be set as follows. The predetermined distance is 10 millimeters. The predetermined time period is 0.5 seconds. Under these conditions, when the fingertip of the operator P penetrates the virtual plane G by the distance X (=15 [mm]) for the time period S (=0.3 [sec]), such a motion by the operator P is determined as a click operation. If the predetermined distance is set to a very short distance, there is possibility that even a subtle motion of the fingertip is recognized as a click operation. Therefore, if the operator P does not like a sensitive response, it is preferable to set the predetermined distance to a reasonable distance.

Figure 6:
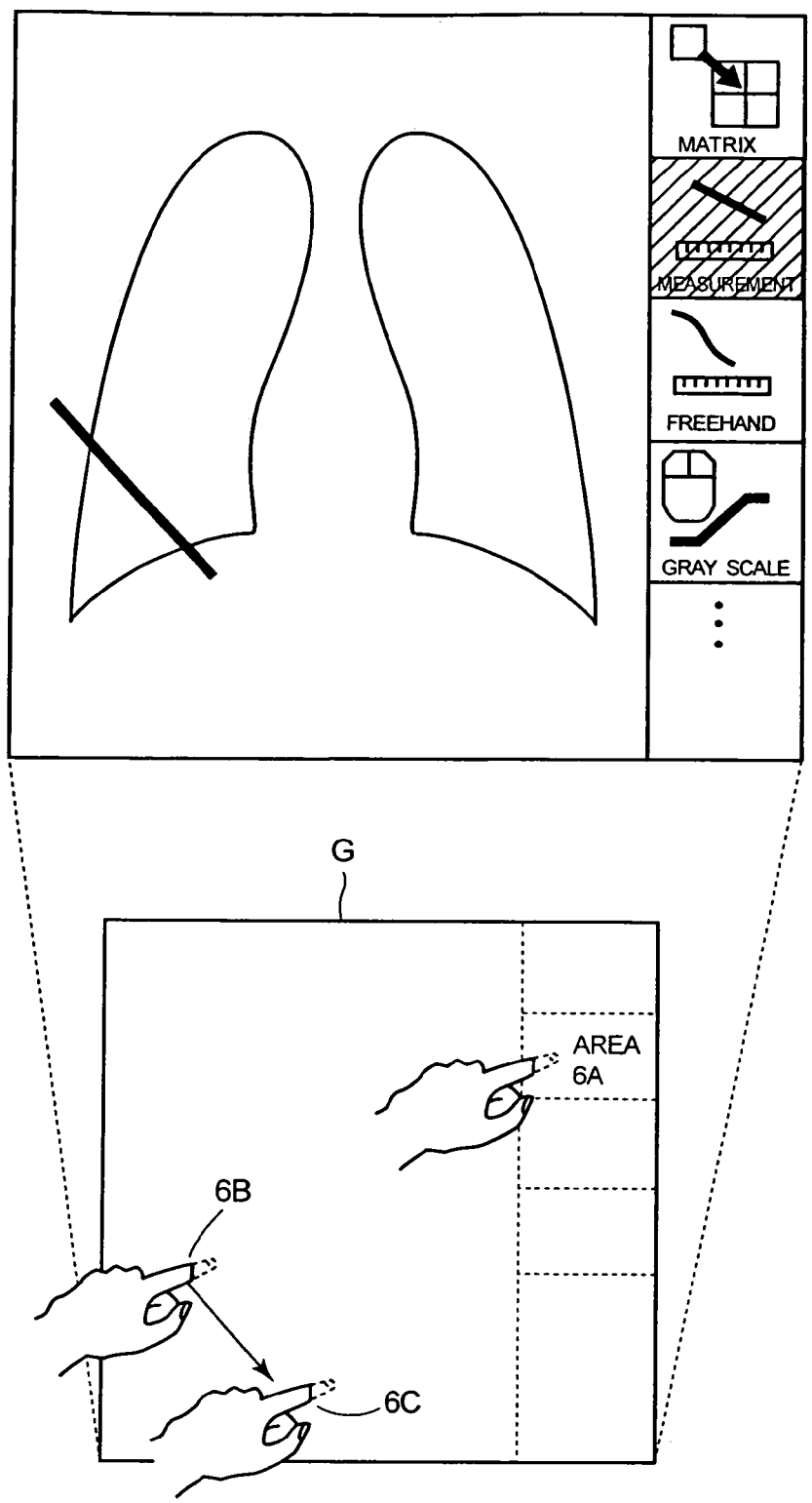
FIG. 6 is an illustration showing an example of a mode selection according to the first embodiment of the present invention.

The click operation is, for example, used to select one of the operation modes described above. FIG. 6 is an illustration showing an example of a mode selection according to the first embodiment of the present invention. As shown in FIG. 6, the operator P brings his or her finger to an area 6A in the virtual plane G and points the area 6A with a fingertip of the finger. Such a pointing motion results in penetrating the virtual plane G and is construed as a click operation as long as the above conditions are met. In response to such a click operation, the distance measurement mode is selected. In the display window, an icon for the distance measurement mode is differentiated from others. The area 6A in the virtual plane G is located at a position corresponding to the icon in the window display. In other words, the operator P looks at the icon and moves his or her fingertip against the icon. This motion results in the click operation in the virtual plane G.

<<Double Click Operation>>

The double click operation is, for example, used to change a matrix size to display a plurality of images. When the click operation is repeated at an interval T within a predetermined time interval, the second processing unit 13f determines that a double click operation has been performed by the operator P. For example, the determination conditions (or thresholds) may be set as follows. The predetermined distance is 10 millimeters. The predetermined time period is 0.3 seconds. Further, the predetermined time interval is 0.5 seconds. Under these conditions, when the fingertip of the operator P penetrates the virtual plane G by the distance X (=15 [mm]) for the time period S (=0.3 [sec]) and repeats a similar motion at the interval (0.4 [sec]), such motions by the operator P are determined as a double click operation.

Figure 7:
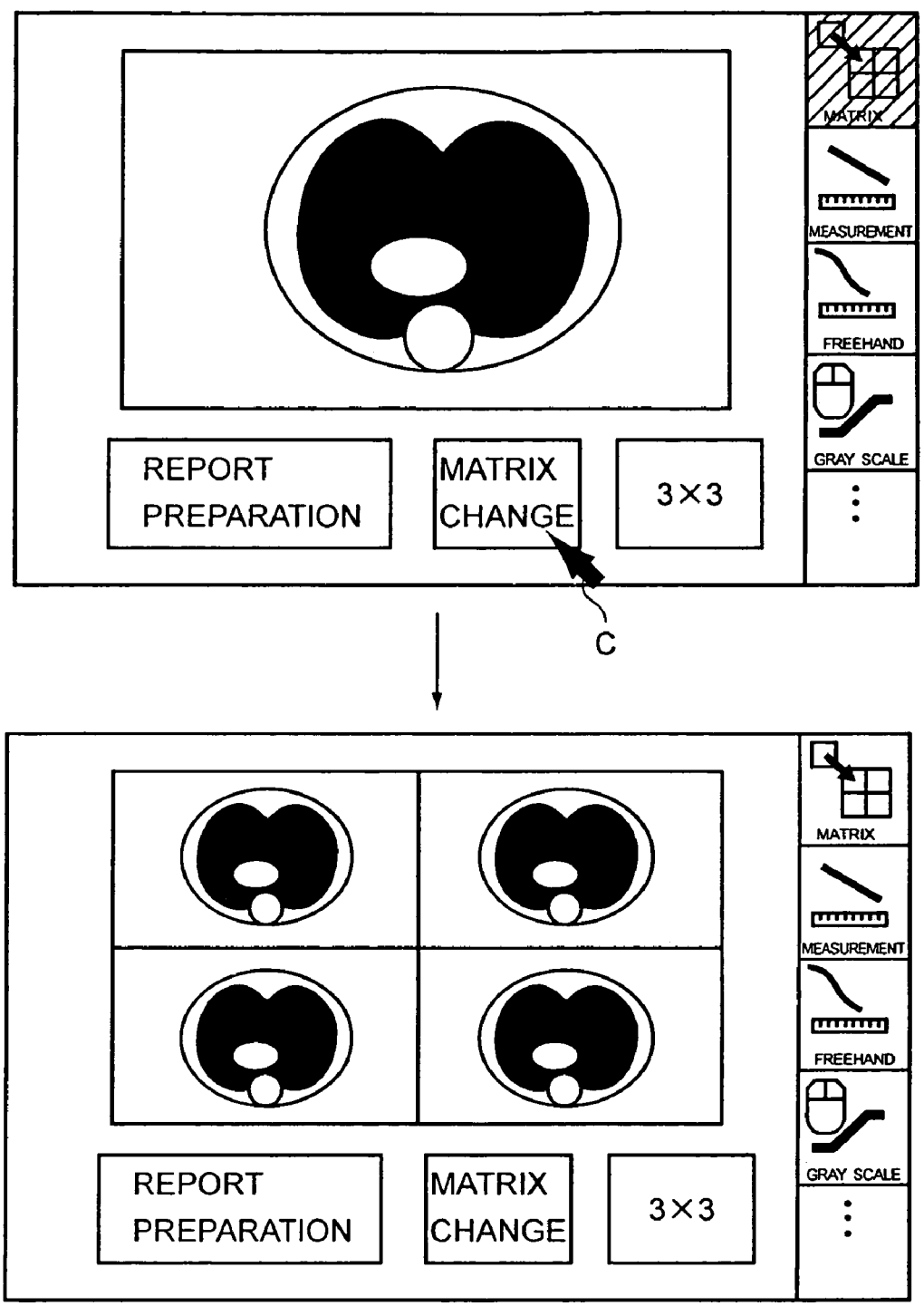
FIG. 7 is an illustration showing an example of a matrix change according to the first embodiment of the present invention.

FIG. 7 is an illustration showing an example of a matrix change according to the first embodiment of the present invention. As shown in FIG. 7, the operator P selects a matrix change mode in a manner similar to the selection of the distance measurement mode. In response to the selection of the matrix change mode, an icon for changing a matrix size is displayed in the display window. As similar to the click operation, the operator P brings his or her fingertip to an area corresponding to the matrix change icon A and points twice against the virtual plane G. Such pointing motions are construed as a double click operation as long as the above conditions are met. In response to such a double click operation, the matrix size is changed. In FIG. 7, the matrix size is changed from 1×1 to 2×2.

The above-described double click operation may alternatively be determined in the following manner. When the click operation is repeated within a second predetermined time period, the second processing unit 13f may determine that a double click operation has been performed by the operator P. For example, the determination conditions (or thresholds) may be set as follows. The predetermined distance is 10 millimeters. The predetermined time period is 0.3 seconds. Further, the second predetermined time period is 1.0 seconds.

In the first embodiment of the present invention, it is possible to display a cursor C in the display window and move the cursor C in accordance with fingertip motions of the operator P. Since it is possible for the controller 13 to track motions of the operator P by processing image data acquired by the video cameras 12a and 12b, motions of the fingertip within a field of view of the virtual plane G from the operator P without penetration are reflected as a cursor move in the display window.

<<Drag Operation>>

The drag operation is, for example, used to draw a desired line in the freehand mode. The second processing unit 13f determines that a drag operation has been performed by the operator P when the following conditions are met. The distance X is more than a predetermined distance. The time period S at an initial penetrating point is more than a predetermined time period. Further, a third time period when the penetration is kept is more than a third predetermined time period. That is, the fingertip is moved in the virtual plane G for more than the third predetermined time period. For example, the determination conditions (or thresholds) maybe set as follows. The predetermined distance is 10 millimeters. The predetermined time period is 0.5 second. Further, the third predetermined time period is 1.0 second. Under these conditions, when the fingertip of the operator P penetrates the virtual plane G by the distance X (=15 [mm]) for the time period S (=1.0 [sec]) and starts to move the fingertip across the virtual plane G for a time period of 2.0 seconds, such a motion by the operator P is determined as a drag operation.

FIG. 8 is an illustration showing an example of a freehand drawing according to the first embodiment of the present invention. As shown in FIG. 8, the operator P selects a freehand mode in a manner similar to the selection of the distance measurement mode. The operator P brings his or her fingertip to a desired initial position in the virtual plane G ((a) in FIG. 8) and moves the fingertip to penetrate the virtual plane G so as to start drawing ((b) in FIG. 8). After the penetration, the operator P moves the fingertip to draw a desired line with the penetration kept by the fingertip ((c) in FIG. 8). Such motions are construed as a drag operation as long as the above conditions are met. To finish the drawing, the operator P withdraws the fingertip from the virtual plane G. Accordingly, a line is drawn in the display window in accordance with the motion of the fingertip as the operator P desires.

If necessary, the drawn line displayed in the display window may be cleared or erased from a part drawn earlier when the length of the drawn line exceeds a predetermined length or when predetermined time has elapsed after such a part was drawn. This can help the drawn line appearing in the display window to be kept within a predetermined length. As an additional feature, when the hand of the operator P penetrates the virtual plane G or when the fingertip penetrates the virtual plane G by a distance longer than the predetermined distance, the hand or the fingertip may be treated as an eraser to clear all or a desired part of the drawn line.

Another example of the drag operation is shown in FIG. 6 again. The drag operation can also be used to measure a distance between two points in the distance measurement mode.

The operator P brings his or her fingertip to a desired first point 6B in the virtual plane G and moves the fingertip to penetrate the virtual plane G so as to determine an initial point. After the penetration, the operator P moves the fingertip to a second point 6C with the penetration kept by the fingertip as to determine an end point. At the second point 6C, the operator P withdraws the fingertip from the virtual plane G. Accordingly, a line corresponding to the line dragged from the first point 6B to the second point 6C in the virtual plane G is displayed in the display window. The distance of the line displayed in the display window is calculated as the distance measurement.

<Flowchart>

A basic operation flow in the image viewer 1 will be described with reference to FIGS. 9 and 10.

Figure 9:
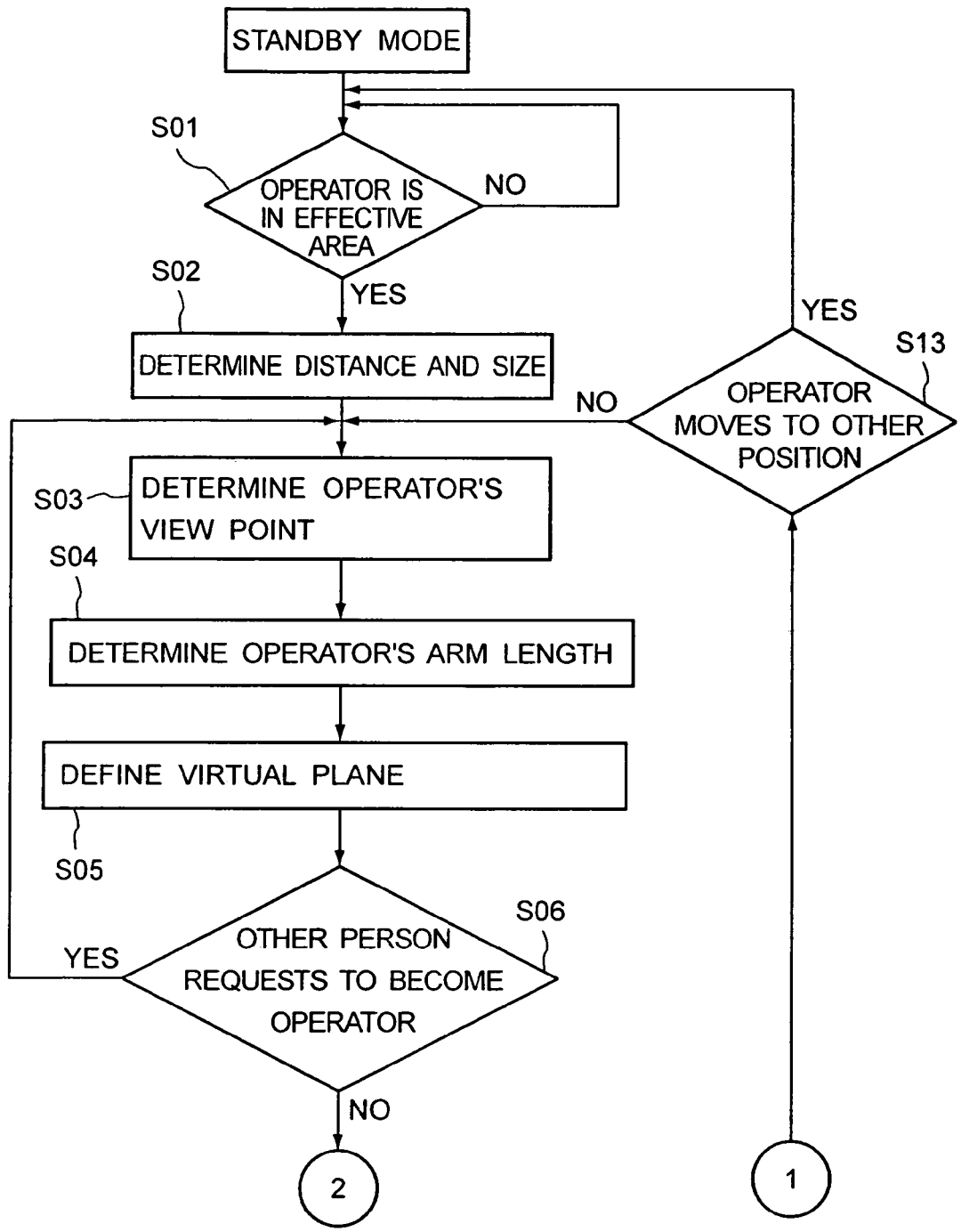
FIG. 9 is a flowchart showing an exemplary flow of operations in the image viewer according to the first embodiment of the present invention.
Figure 10:
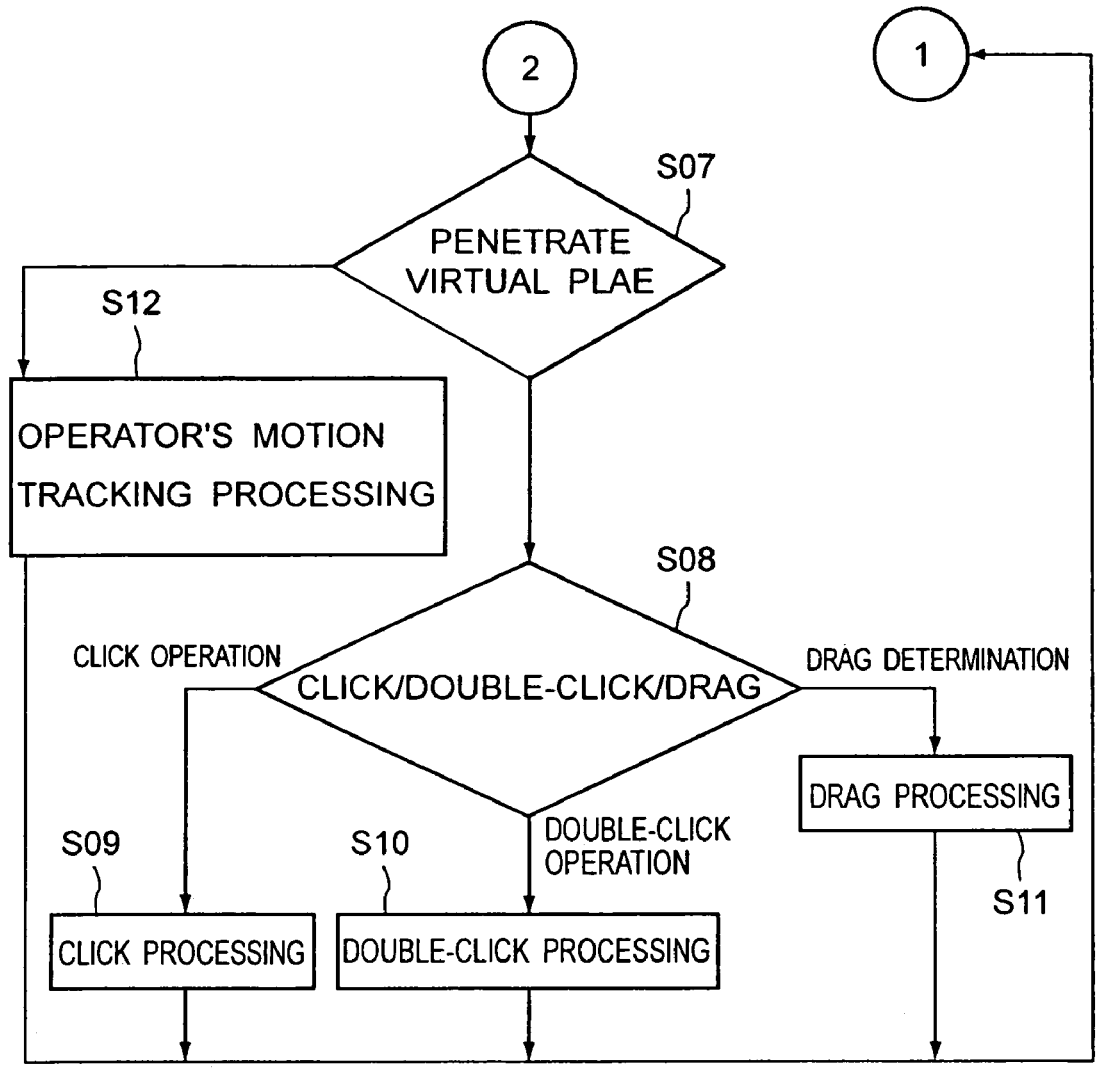
FIG. 10 is a flowchart showing an exemplary continued flow of that shown in FIG. 9 according to the first embodiment of the present invention.

FIG. 9 is a flowchart showing an exemplary flow of the operations in the image viewer 1 according to the first embodiment of the present invention. FIG. 10 is a flowchart showing an exemplary continued flow of that shown in FIG. 9 according to the first embodiment of the present invention.

During a standby mode, when the operator P enters into the predetermined effective area described before, the video cameras 12a and 12b acquire image data of the operator P. The recognition unit 13a recognizes based on the acquired image data that the operator P has entered into the predetermined effective area (step S01). The information acquisition unit 13g determines a distance between the screen 11 and the operator P. The information acquisition unit 13g also determines a size of the display window projected to the screen 11 (step S02)

When the image viewer 1 requires an authority for operating the image viewer 1 to the operator P, the operator P shows his or her hand in the predetermined effective area. The recognition unit 13a recognizes the hand shape of the operator P and determines that the operator P is authorized to operate the image viewer 1. Alternatively, when the operator P utters a predetermined word in voice, the voice is collected as speech data through a microphone which may be provided in the video cameras 12a and 12b. The recognition unit 13a recognizes the predetermined word based on collected speech data and determines that the operator P is authorized to operate the image viewer 1.

The recognition unit 13a then determines a view point of the operator P. The view point can be set to an opening eye when the operator P opens only one eye. When the operator P opens both eyes, a dominant eye of the operator P can be set as the view point (step S03). In response to the view point determination, the recognition unit 13a implements calculations for obtaining, for example, a height of the view point, a distance between the view point and the screen 11, and a distance between the recognized hand and the screen 11.

The first processing unit 13b determines the arm length of the operator P based on the acquired image data, the view point, and the calculated distances (step S04). The first processing unit 13b determines a position in a distance L of a half length of the operator P's arm from the view point. The virtual plane G is defined at the position in the distance L from the view point (step S05).

After the definition of the virtual plane G, the recognition unit 13a determines whether there is other operator P who is showing his or her hand in order to obtain an authority for operating the image viewer 1 (step S06). When it is determined that there is such other operator P in step S06, steps S03 to S05 are repeated for this new operator P.

The first processing unit 13b determines whether the fingertip of the operator P penetrates the virtual plane G or not (step S07) If it is determined that the fingertip penetrates the virtual plane G, various parameters described before including one or more of the distance X, the time period S, the time interval, the second time period, and the third time period are determined and compared to the corresponding predetermined values. As a result of the comparison, the operation against the virtual plane G is determined whether it is a click operation, a double click operation, or a drag operation (step S08).

The third processing operation 13h implements processing in accordance with the determined operation. When it is the click operation, the third processing unit 13h implements click processing (step S09). When it is the double click operation, the third processing unit 13h implements double click processing (step S10). When it is the drag operation, the third processing unit 13h implements drag processing (step S11).

When it is not determined that the fingertip penetrates the virtual plane Gin step S07, the motion of the operator P is tracked by processing image data acquired by the video cameras 12a and 12b. Accordingly, motions of the fingertip within a field of view of the virtual plane G from the view point without penetration are reflected as a cursor move in the display window (step S12). The third processing unit 13h may implement the reflecting display processing based on the view point and information including a position and a size of the display window projected to the screen 11.

After the processing in step S09, S10, S11, or S12, the operation continues to step S13. In step S13, the recognition unit 13a determines whether the operator P moves to the outside of the predetermined effective area or not (step S13). When the recognition unit 13a cannot recognize the operator P within image data based on the image processing of the image data, it is determined that the operator P has moved to the outside of the predetermined effective area. When such a determination is made, it is determined that the operation of the image viewer 1 through the virtual plane G has been terminated. Accordingly, the operation returns to step S01. On the other hand, when the recognition unit 13a still recognizes the operator P within the image data, the operation returns to step S03 so that the view point is determined again or corrected, if necessary, for the next operation.

Figure 11:
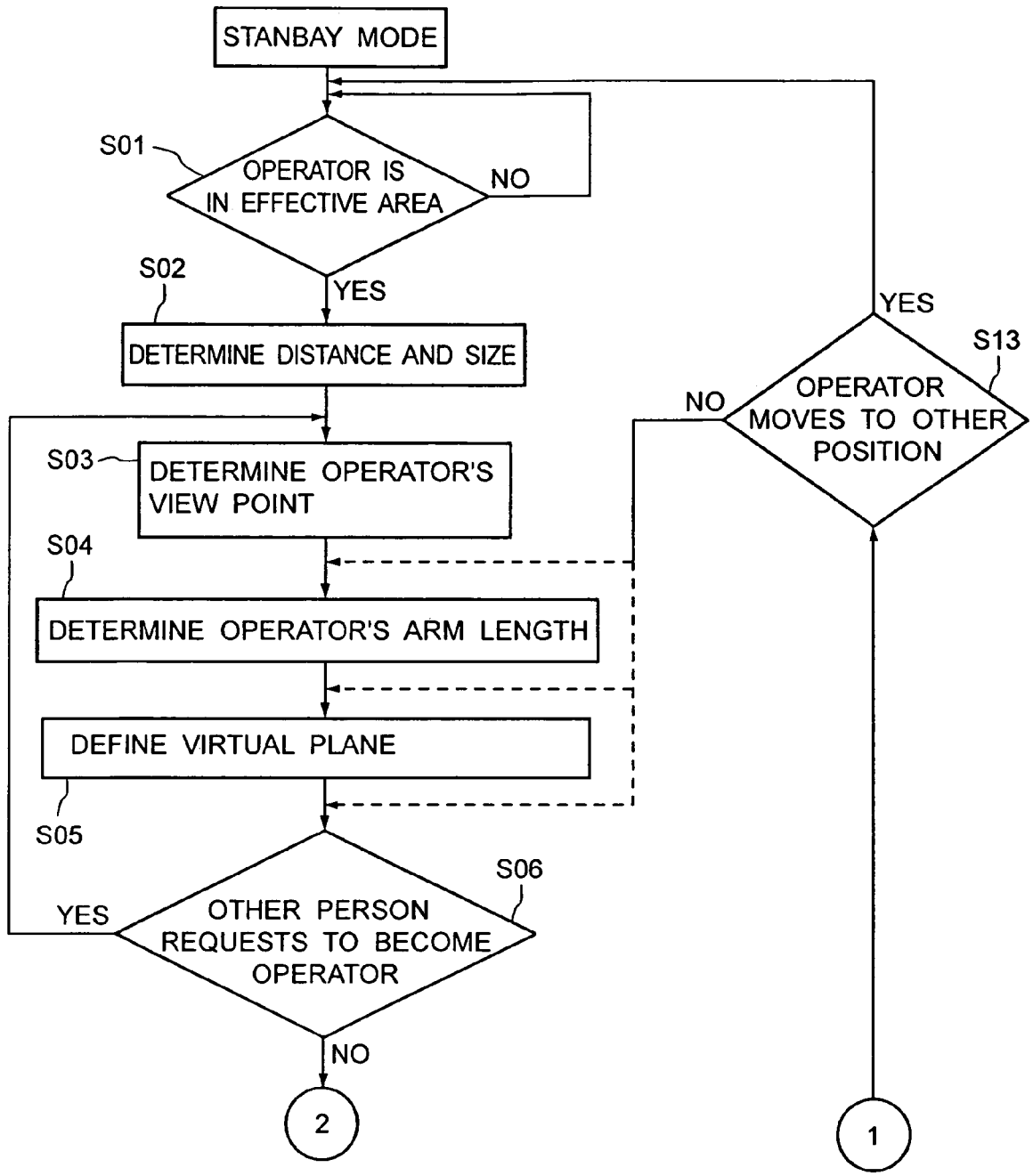
FIG. 11 is a flowchart showing a modified example of the flowchart shown in FIG. 9 according to the first embodiment of the present invention.

As an alternative operation flow in case that there recognition unit 13a still recognizes the operator P within the image data in step S13, the operation may return to step S04 as shown in FIG. 11. This is possible when the view point of the operator P is kept tracked during the processing in step S09, S10, S11, or S12. Further, the operation may return to step S05 from step S13 as shown in FIG. 11, instead. This is possible when the previously acquired data regarding the arm length of the operator P is kept in the recognition unit 13a or in the first storage unit 13c, in addition to the view point tracking. Still further, the operation may alternatively return to step S06 from step S13 as shown in FIG. 11. This is possible when it is not necessary to redefine the virtual plane G, in addition to the view point tracking and the arm length data.

As described above, the image viewer 1 according to the first embodiment recognizes the operator P in accordance with the shape of the operator P's hand or any recognizable performance by the operator P. Further, the image viewer 1 defines the virtual plane G and the virtual keyboard which correspond to a keyboard, a mouse, and the like at an appropriate position for the operator P in the space. Therefore, the operator P does not need to hand over an operation unit such as the keyboard and/or the mouse to other operators. Accordingly, the operator P does not need to consider hygienic matters. This helps to improve the performance of the operator P.

According to the first embodiment, the virtual plane G has been positionally defined at a distance half the length of operator P' arm from the viewpoint. The virtual plane G may, however, be defined at a position in a predetermined distance on the basis of a hand of the operator P. In this case, the virtual plane G may be defined in parallel with a palm of the hand.

Also according to the first embodiment, the recognition unit 13a and the second processing unit 13f have acquired information including the height of the view point of the operators eye, which of the operators eyes is her/his dominant eye, hand positions of the operator P, the distance between the screen 11 and the view point, the size of the display window projected to the screen 11, and the like. Regarding such information, however, standard values may be stored in the recognition unit 13a and/or the second processing unit 13f in advance.

Further, the recognition unit 13a has determined that the operator P is authorized to operate the image viewer 1 when the operator P has shown his or her hand or when the operator P has uttered the predetermined word in voice. Even when, however, the operator P enters into the predetermined effective area in order to operate the image viewer 1 without a separate advance instruction, the recognition unit 13a may determine that the operator P is authorized to operate the image viewer 1. The recognition unit 13a may alternatively determine that the operator P who first enters into the predetermined effective area is authorized to operate the image viewer 1.

Still further, the third processing unit 13h may adjust sizes and/or thickness of lines, figures, and characters to be drawn or displayed in the display window projected to the screen 11. Such adjustment may be based on a distance between the screen 11 and the view point of the operator P.

The video camera may be provided at any position(s). Instead of the positions described in the first embodiment, for example, the video camera can be provided behind the screen 11 and acquire image data through a small hole provided in the screen 11. The video camera may be provided at the top or the bottom of the screen 11. Mixed positions of those may also applicable to the first embodiment. Any number of video cameras can be provided wherever the position is.

<Virtual Plane Position>

Figure 12:
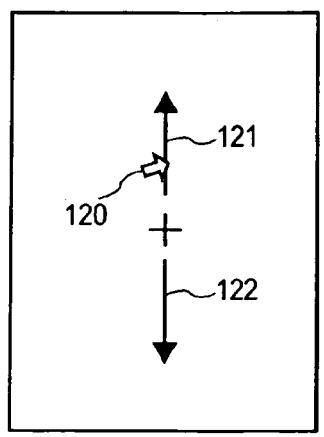
FIG. 12 is an illustration showing an example of a virtual plane position change window according to the first embodiment of the present invention.

When the operator P feels like changing the currently defined position of the virtual plane G, the operator P can input operational commands to display a virtual plane position change window. FIG. 12 is an illustration showing an example of the virtual plane position change window according to the first embodiment of the present invention. For example, if the operator P moves a cursor 120 following motions of the fingertip onto an upward arrow 121 in the virtual plane position change window, the virtual plane G is defined at a position closer to the operator P. If the operator P moves the cursor 120 onto a downward arrow 122 in the virtual plane position change window, the virtual plane G is defined at a position further from the operator P.

Figure 13:
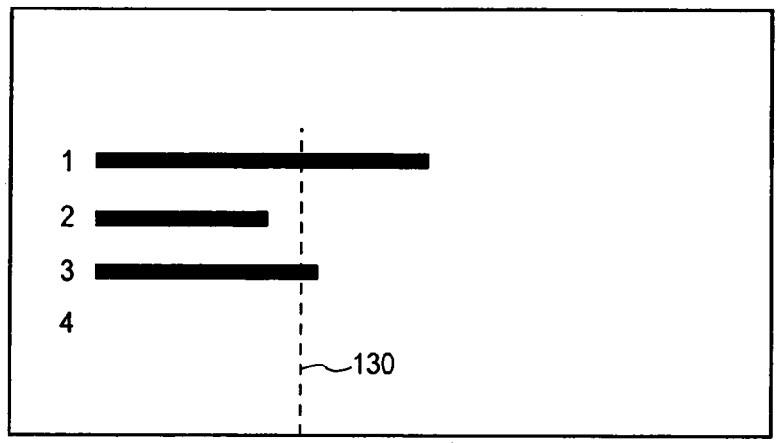
FIG. 13 is an illustration showing a first example of a penetration test window according to the first embodiment of the present invention.

After the position change of the virtual plane G or any time the operator desires, the operator P can try to see where the virtual plane G is defined and how much the fingertip penetration is required for a click operation. FIG. 13 is an illustration showing a first example of a penetration test window according to the first embodiment of the present invention. As shown in FIG. 13, when the operator P tried the penetration against the virtual plane G for the first time, the first penetration distance has shown that the fingertip penetrates the virtual plane G too much. A dashed line 130 indicates a threshold distance point for recognizing a click operation. The dashed line 130 may indicate a position where the virtual plane G is defined. In response to the attempt, the second attempt has shown that it is a little short. Finally, in the third attempt, the operator P can recognize how much to move the fingertip as to be recognized as a click operation. The dashed line 130 can be moved according to changes of the predetermined distance described before.

Figure 14:
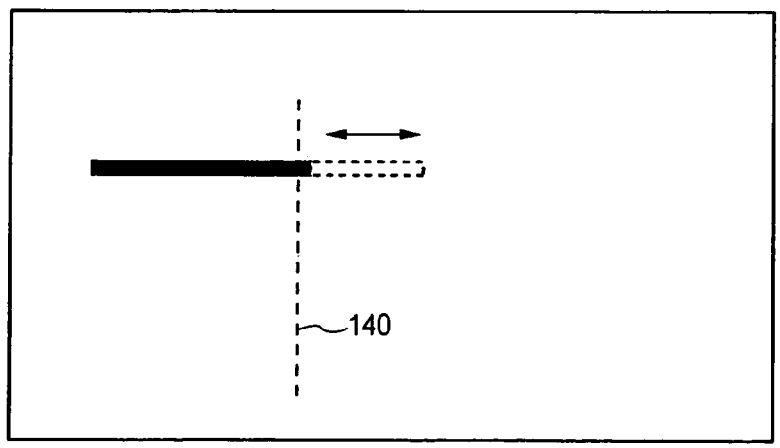
FIG. 14 is an illustration showing a second example of the penetration test window according to the first embodiment of the present invention.

An alternative penetration test window is shown in FIG. 14. FIG. 14 is an illustration showing a second example of the penetration test window according to the first embodiment of the present invention. In the second example, the penetration test window shows only one indicator which changes its length in accordance with the motion of the fingertip against the virtual plane G. Therefore, the operator P can easily comprehend to what extent the operator P should move his or her fingertip for a click operation. A dashed line 140 indicates the same as the dashed line 130 in FIG. 13.

Second Embodiment

Figure 15:
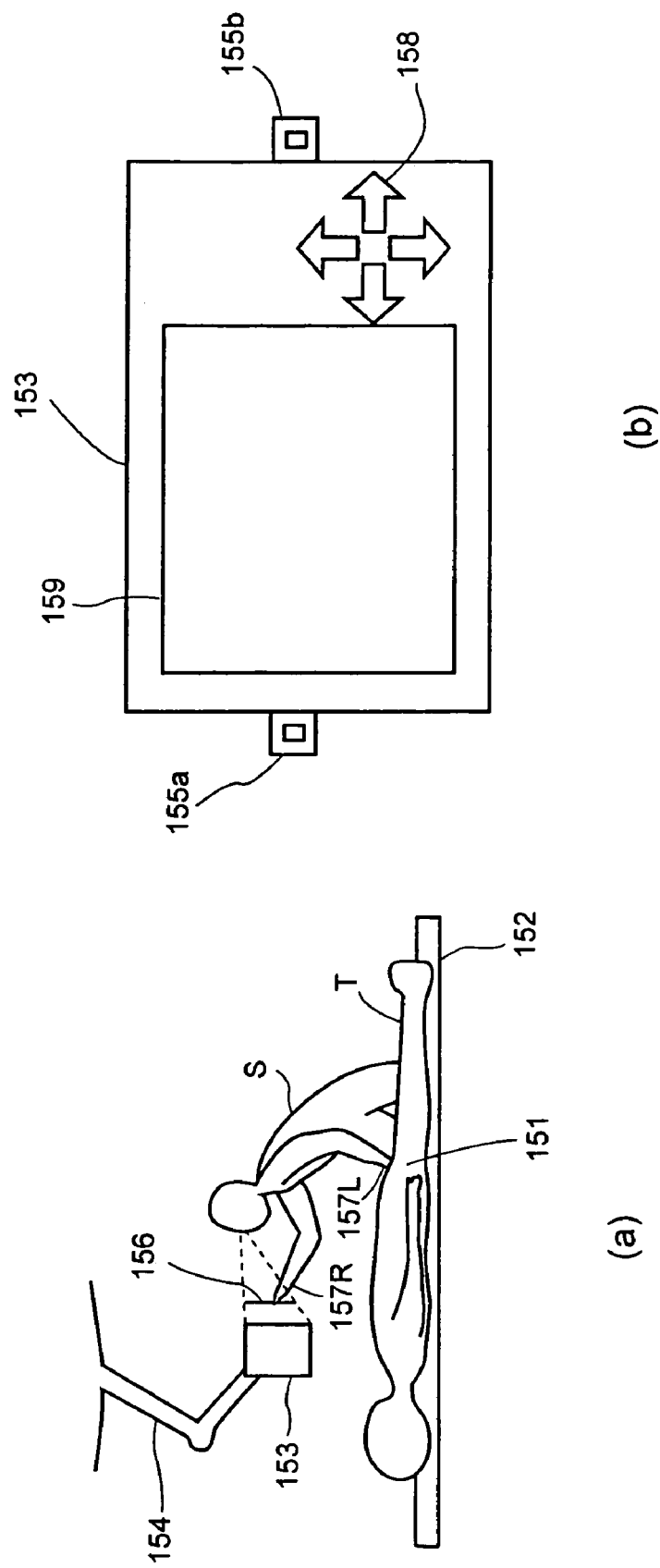
FIG. 15 is an illustration showing an example of a fluoroscopy position change through a virtual plane according to a second embodiment of the present invention.

A second embodiment of the present invention will regard of an X-ray fluoroscopy position change during a catheter operation as another example of the use of a virtual plane. FIG. 15 is an illustration showing an example of such a fluoroscopy position change through a virtual plane according to the second embodiment of the present invention.

FIG. 15(a) shows that a doctor S is inserting a catheter into a patient T from the inguina 151. The patient T is lying on a bed 152 which is a part of an X-ray diagnosis apparatus. During the catheter insertion, the X-ray diagnosis apparatus acquires fluoroscopic image data of the patient T. The fluoroscopy is implemented over a body part of the patient T where a head of the catheter is located. Fluoroscopic images based on the acquired image data are displayed by a display monitor 153 so that the doctor S can make visually verify through the display monitor 153 that the insertion is correctly being performed. The display monitor 153 is supported by a supporter 154.

As shown in FIG. 15(b), video cameras 155a and 155b are provided at both sides of the display monitor 153. The video cameras 155a and 155b acquire image data of the doctor S. Motions of the doctor S are tracked by image processing performed on the acquired image data. Such image processing is implemented in an image processing unit (not shown). The image processing unit may be provided in or independently from the X-ray diagnosis apparatus. A control unit (not shown) controls an arm position of the X-ray diagnosis apparatus based on a result of the image processing so as to change a fluoroscopy position. The arm supports an X-ray tube and an X-ray detector. The control unit may be provided in or independently from the X-ray diagnosis apparatus. The fluoroscopy position change depends on an operation by the doctor S against a virtual plane 156.

The virtual plane 156 is, for example, defined in between a view point of the doctor S and the display monitor 153. When the fingertip of the doctor S penetrates the virtual plane 156 for a click operation, the image processing unit recognizes such an operation by processing image data acquired through the video cameras 155a and 155b. Accordingly, the control unit controls the arm position in accordance with the click operation.

The virtual plane 156 may, for example, be defined within an extension from a view point of the doctor S to each corner of the display monitor 153. The size of the virtual plane 156 may be within a field of view from the view point to the monitor display 153 as shown in FIG. 15(a).

The doctor S can change the arm position by using one hand 157R (e.g., a right hand) so as to change a fluoroscopic image displayed in the display monitor 153 while the doctor S is holding the catheter in another hand 157L (e.g., a left hand). When a fingertip of the one hand 157R penetrates the virtual plane 156 by a clicking operation such as a pressing motion, the image processing unit recognizes such an operation. For example, four-direction arrows 158 are displayed in the display monitor 153. If the fingertip penetrates the virtual plane 156 at a position corresponding to an upward arrow of the four-direction arrows 158, the arm position is controlled to slightly move towards a head of the patient T. Similarly, if the fingertip penetrates the virtual plane 156 at a position corresponding to a downward arrow of the four-direction arrows 158, the arm position is controlled to slightly move towards a foot of the patient T. Further, if the fingertip penetrates the virtual plane 156 at a position corresponding to a leftward arrow of the four-direction arrows 158, the arm position is controlled to slightly move towards a right side of the patient T. Finally, if the fingertip penetrates the virtual plane 156 at a position corresponding to a rightward arrow of the four-direction arrows 158, the arm position is controlled to slightly move towards a left side of the patient T. Fluoroscopic images based on image data acquired at the changed position of the arm are displayed in an image display window 159 of the monitor display 153.

The four-direction arrows 158 indicate only four directions. Instead of the four-direction arrows 158, however, more directions (e.g., eight directions) may be displayed in arrows. The move distance in one click operation may be either fixed or set in a variable manner.

Instead of the click operation against the four-direction arrows 158, the doctor S may perform a drag operation against the virtual plane 156. When the fingertip of the one hand 157R penetrates the virtual plane 156 for the drag operation, the image processing unit recognizes such an operation. If the doctor S performs a drag operation upward, the arm position is controlled to slightly move towards the head of the patient T. Similarly, if the doctor S performs a drag operation downward, the arm position is controlled to slightly move towards the foot of the patient T. Further, if the doctor S performs a drag operation leftward, the arm position is controlled to slightly move towards the right side of the patient T. Finally, if the doctor S performs a drag operation rightward, the arm position is controlled to slightly move towards the left side of the patient T. Fluoroscopic images based on image data acquired at the changed position of the arm are displayed in the image display window 159.

The move distance may be fixed regardless of the distance of the drag operation. Alternatively, the move distance may be variable in accordance with the distance of the drag operation. For example, when the arm moves by a first distance in response to the drag operation by up to three centimeters, the arm may move by twice the first distance in response to the drag operation by more than three centimeters. The move direction of the arm may include directions other than the above-described four directions in accordance with the drag operation.

In the case of the second embodiment, the doctor S could inadvertently move his arm through the virtual plane while not intending to operate the display monitor 153. That is, although the display monitor 153 is directly operated through the virtual plane 156, the display monitor 153 is not a directly purposed object in the movement of the doctor S's arm. However, such an indirect object like the display monitor 153 is construed as an object to be operated in the understanding of a scope of the present invention as long as the direct object cannot respond without instructions from the indirect object when an operation is made through a virtual plane.

According to the system in the second embodiment, the doctor S does not have to ask someone else to adjust a position of his/her arm. When the doctor S would like to have a view currently not displayed, of the patient T for the catheter insertion, the doctor S can perform the adjusting operation without touching anything for himself or herself. In addition, no hygienic problem occurs in the doctor's operation.

One or more of the features described in the first embodiment may be applicable to the second embodiment.

Third Embodiment

Figure 16:
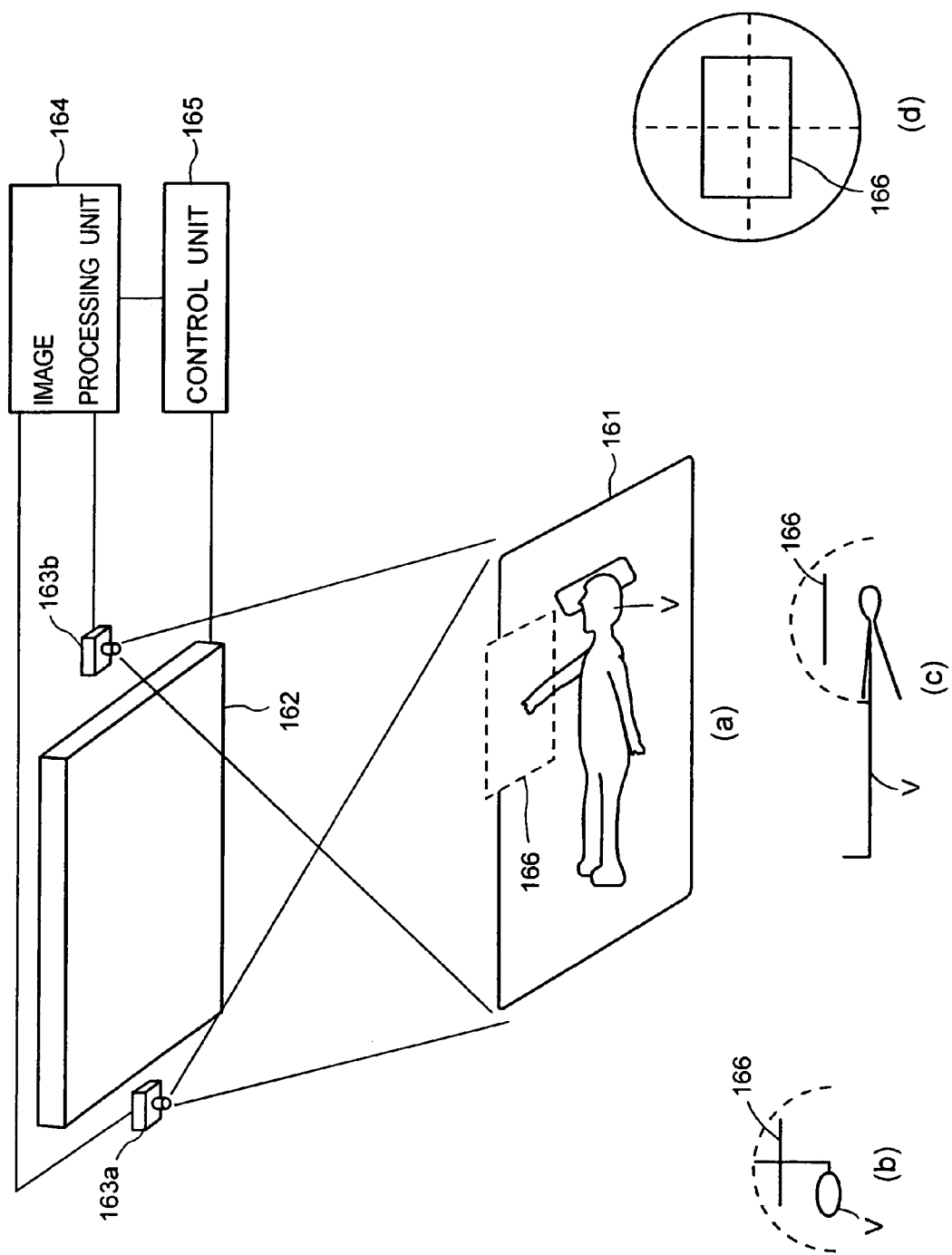
FIG. 16 is an illustration showing an example of a switching through a virtual plane according to a third embodiment of the present invention.

Operations through a virtual plane are also applied to other fields in everyday life. The virtual plane could be used to control any appliances that normally require physical manipulation to operate. Examples of such appliances might include, but not limited to: lighting fixtures, windows, heating systems, doors, stoves, and various other items capable of being controlled. A third embodiment of the present invention will regard of switching on/off of a fluorescent light fixed to a ceiling as one example. FIG. 16 is an illustration showing an example of such a switching through a virtual plane according to the third embodiment of the present invention.

As shown in FIG. 16(a), a user V is lying on a bed 161. In a room where the user V is lying, a fluorescent light 162 is fixed to a ceiling of the room. Similar to the first embodiment, there are provided video cameras 163a and 163b at both sides of the fluorescent light 162. The video cameras 163a and 163b acquire image data of the user V. Motions of the user V are tracked by image processing on the acquired image data. Such image processing is implemented in an image processing unit 164. A control unit 165 controls the switching on and off of the fluorescent light 162 based on a result of the image processing. The switching depends on an operation by the user V against a virtual plane 166.

The virtual plane 166 is, for example, defined in between a viewpoint of the user V and the fluorescent light 162. When the hand or the arm of the user V penetrates the virtual plane 166 for a click operation, the image processing unit 164 recognizes such an operation by processing image data acquired through the video cameras 163a and 163b. Accordingly, the control unit 165 controls to switch on/off the fluorescent light 162.

A size of the virtual plane 166 may, for example, be determined at a predetermined position as shown in figures (b) to (d) in FIG. 16. When the virtual plane 166 is formed of a quadrangle, one side of the virtual plane 166 may be determined within a reach of an arm of the user V in a direction from the left to the right of the user V as shown in FIG. 16(b). Similarly, another side of the virtual plane 166 may be determined within a reach of an arm of the user V in a direction from the foot to the head of the user V as shown in FIG. 16(c). FIG. 16(d) shows one exemplary size of the virtual plane 166 viewed from the video cameras 163a and 163b. The virtual plane 166 may alternatively be formed of a circle, a triangle, or any other shape.

One or more of the features described in the first embodiment may be applicable to the third embodiment.

Fourth Embodiment

Figure 17:
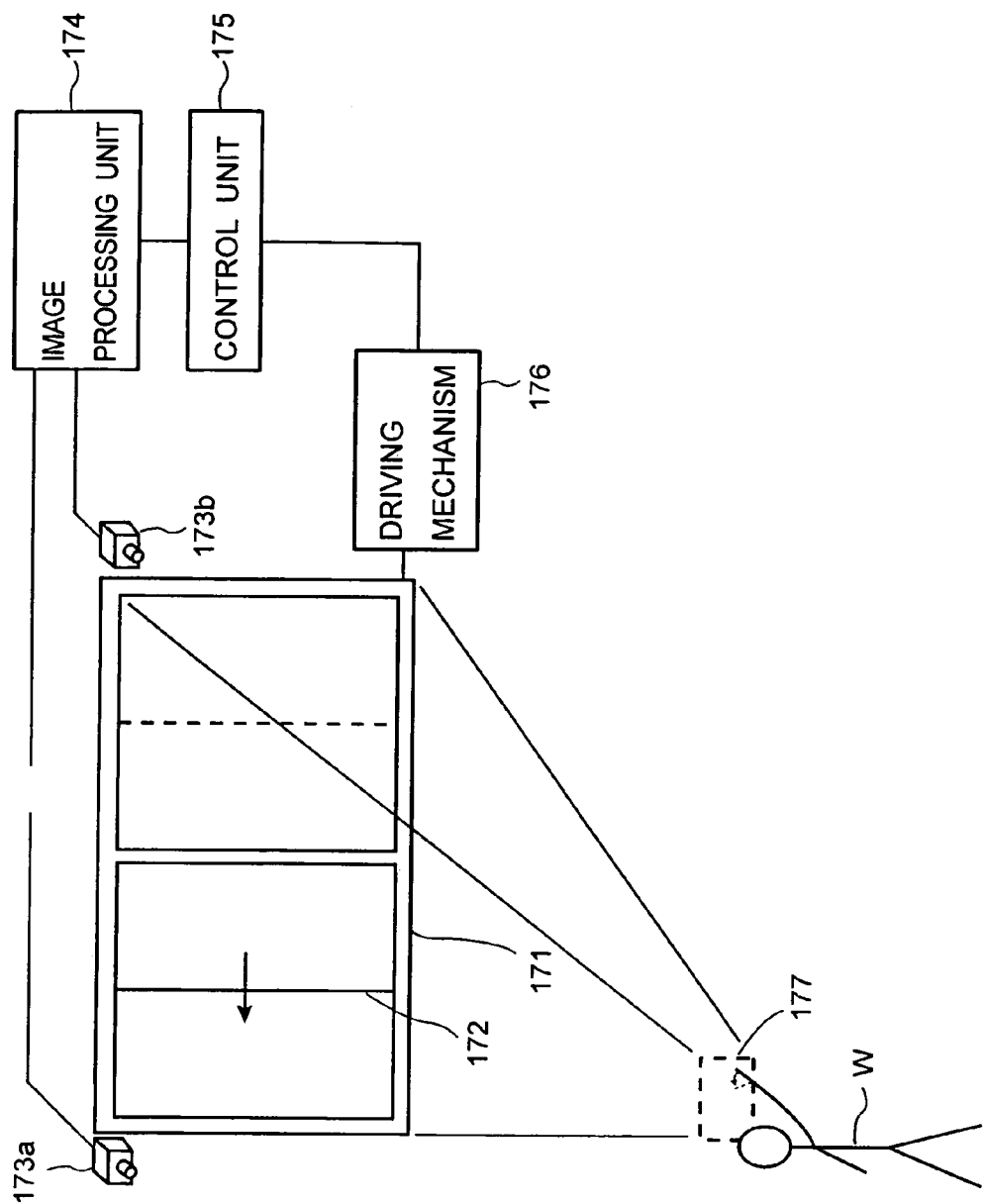
FIG. 17 is an illustration showing an example of a window opening and closing through a virtual plane according to a fourth embodiment of the present invention.

A fourth embodiment of the present invention will regard of opening and closing a window. FIG. 17 is an illustration showing an example of such a window opening and closing through a virtual plane according to the fourth embodiment of the present invention.

As shown in FIG. 17, a user W is located in front of a window 171 which may be provided in an office or a house. The window 171 has windowpanes 172. Similar to the second embodiment, there are provided video cameras 173a and 173b at both sides of the window 171. The video cameras 173a and 173b acquire image data of the user W. Motions of the user w are tracked by image processing on the acquired image data. Such image processing is implemented in an image processing unit 174. A control unit 175 provides control signals to a driving mechanism 176 based on a result of the image processing. The driving mechanism 176 drives to open one of the windowpanes 172 in response to the control signals. The driving mechanism 176 also drives to close the one windowpane 172 in response to the control signals. The control signals depend on an operation by the user W against a virtual plane 177.

The virtual plane 177 is, for example, defined in between a view point of the user W and the window 171. When the user W penetrates his or her fingertip against the virtual plane 177 for a drag operation, the image processing unit 174 recognizes such an operation by processing image data acquired through the video cameras 173a and 173b. Accordingly, the control unit 175 controls the driving mechanism 176. When the user W performs a drag operation towards the left in FIG. 17, the windowpane 172 is driven by the driving mechanism 176 and moves to the left for closing. Similarly, when the user W performs a drag operation towards the right in FIG. 17, the windowpane 172 is driven by the driving mechanism 176 and moves to the right for opening.

The virtual plane 177 may, for example, be defined within an extension from the view point of the user W to each corner of the window 171.

One or more of the features described in the first embodiment maybe applicable to the fourth embodiment.

When there are, for example, two appliances at different distance positions from a user, the two appliances may be controlled (or operated) depending on penetration distances against a virtual plane. For, example, when the virtual plane is penetrated by one centimeter, a nearer one of the two appliances is operated. The other one is operated when the virtual plane is penetrated by three centimeters. Alternatively, a plurality of virtual planes may be prepared according to the number of appliances in different distances. Further, even for a single appliance, different operations of the appliance may be assigned to different penetration distances or a plurality of virtual planes, respectively.

In the embodiments described above, video cameras have been described for obtaining image data of the operator, the user, or the doctor. However, other types of cameras may alternatively be used as long as the cameras can sequentially obtain at least a predetermined number of images (or pictures) in a predetermined time period. A WEB camera and a digital camera are examples of such cameras, in addition to the video camera.

The penetration against a virtual plane is not limited to a performance by a fingertip of an operator, but may also be performed by any predetermined part of the operator.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An operation recognition system, comprising:
an object to be operated;
at least one camera configured to acquire image data of an operator, at least a predetermined number of image data being acquired in a predetermined time period;
a processor configured to perform recognition processing on the acquired image data, so as to define a first virtual plane in between the object and the operator, and to determine if a predetermined part of the operator penetrates the first virtual plane by more than a variable predetermined length; and
a controller configured to control the object based on the determination.

2. The system according to claim 1, wherein the processor is configured to recognize a predetermined motion of the operator and the controller is operative when the processor recognizes the predetermined motion of the operator.

3. The system according to claim 1, wherein the processor is configured to recognize a predetermined voice of the operator and the controller is operative when the processor recognizes the predetermined voice of the operator.

4. The system according to claim 1, wherein the processor is configured to recognize an operational authority of the operator based on the recognition processing.

5. The system according to claim 1, wherein the processor is further configured to detect a part of the first virtual plane penetrated by the predetermined part of the operator, and wherein the controller controls the object based on the detection.

6. The system according to claim 1, wherein, when the processor is configured to recognize an eye of the operator as a view point, and to define the first virtual plane between the object and the view point.

7. The system according to claim 1, wherein, when the processor is configured to recognize a length of an operator's arm, and to define the first virtual plane at a position within the recognized length from the operator.

8. The system according to claim 1, wherein the first virtual plane is defined at a variable position based on the recognition.

9. The system according to claim 1, wherein the processor is configured to determine a penetration when the predetermined part of the operator penetrates the first virtual plane for more then a predetermined period.

10. The system according to claim 9, wherein the predetermined period is variable.

11. The system according to claim 1, wherein the controller is configured to control the object based on a length by and a time period in which the predetermined part of the operator penetrates the first virtual plane.

12. The system according to claim 1, wherein the object includes a display configured to display one or more operation items, and wherein the controller is configured to control the implementation of one of the operation items based on the recognition and the determination.

13. The system according to claim 12, wherein the processor is configured to recognize a predetermined motion of the operator, and the processor is configured to determine that the predetermined motion represents a click operation.

14. The system according to claim 12, wherein the processor is configured to recognize a predetermined motion of the operator, and the processor is configured to determine that the predetermined motion represents a double-click operation.

15. The system according to claim 11, wherein the processor is configured to recognize a predetermined motion of the operator, and the processor is configured to determine that the predetermined motion represents a drag operation.

16. The system according to claim 1, further comprising a second object configured to operate in response to the operation of the object.

17. The system according to claim 1, wherein the processor is further configured to define a virtual keyboard in the first virtual plane, and wherein the controller is configured to control the object in relation to a keyboard input via the virtual keyboard based on the determination.

18. The system according to claim 17, wherein the object includes a display configured to display a keyboard image corresponding to the virtual keyboard, and wherein the keyboard image distinguishes a key corresponding to the keyboard input through the virtual keyboard.

19. The system according to claim 1, wherein the processor is further configured to define a second virtual plane different from the first virtual plane and a virtual keyboard in the second virtual plane and to determine if a predetermined part of the operator penetrates the second virtual plane based on the recognition, and wherein the controller is configured to control the object in relation to a keyboard input via the virtual keyboard based on the determination.

20. The system according to claim 19, wherein the object includes a display configured to display a keyboard image corresponding to the virtual keyboard, and wherein the keyboard image distinguishes a key corresponding to the keyboard input through the virtual keyboard from the other keys.

21. The system according to claim 1, wherein the object includes a display configured to display one or more operation items, the display including a projector and a screen, wherein the first virtual plane is defined in between the screen and the operator.

22. The system according to claim 1, wherein the object includes a medical apparatus.

23. The system according to claim 22, wherein the medical apparatus comprises:
a display monitor configured to display one or more operation items; and
a radiography device configured to radiograph a specimen, wherein the controller is configured to control the implementation of one of the operation items based on the determination, and wherein the radiography device is configured to be controlled in response to the implementation of the said one of the operation items.

24. The system according to claim 23, wherein a position of the radiography device is configured to be controlled when a catheter is operated by the operator.

25. The system according to claim 1, wherein the object includes an appliance.

26. The system according to claim 1, further comprising a display configured to display an indicator indicating how much the predetermined part of the operator penetrates the first virtual plane.

27. The system according to claim 26, wherein the indicator varies in accordance with a motion of the predetermined part of the operator.

28. The system according to claim 1, wherein the object includes a display configured to display a virtual plane position change window and a position of the first virtual plane is changed in accordance with the determination.

29. An image display apparatus for displaying an image, the apparatus comprising:
- a display configured to display the image in a screen;
- a position detector configured to detect a position of an operator and a position of an operator's hand;
- a virtual plane defining mechanism configured to define a virtual plane in between the screen and the operator based on the position of the operator;
- a determining mechanism configured to determine a virtual contact between the virtual plane and the operator's hand based on the position of the operator's hand and a position of the virtual plane when the operator's hand penetrates the virtual plane by more than a variable predetermined length; and
- a display control mechanism configured to control a display of the image based on determination by the determining element.

30. The apparatus according to claim 29, further comprising a shape detector configured to detect a shape of the operator's hand; and
- a recognition mechanism configured to recognize that the operator has an operation authority when the detected shape is identical to a predetermined shape.

31. An image display apparatus for displaying an image, comprising:
- a display configured to display the image in a screen;
- imaging elements provided at both sides of the screen and configured to acquire image data from different directions;
- a position detector configured to detect a position of an operator relative to the screen and a position of an operator part based on the acquired image data;
- a virtual plane defining mechanism configured to define a virtual plane in between the screen and the operator based on the position of the operator;
- a determining mechanism configured to determine a virtual contact manner between the virtual plane and the operator part based on the position of the operator part and a position of the virtual plane when the operator part penetrates the virtual plane by more than a variable predetermined length; and
- a display control mechanism configured to determine an operation item corresponding to the contact manner based on determination by the determining mechanism and to control a display of the image according to the operation item.

32. A method of controlling an object, the method comprising steps of:
- acquiring a predetermined number of image data of an operator in a predetermined time period;
- performing recognition processing on the acquired image data;
- defining a virtual plane in between the object and the operator;
- determining if a predetermined part of the operator penetrates the virtual plane by more than a variable predetermined length; and based
- on the recognition processing; and
- controlling the object based on the determination.

33. The method according to claim 32, wherein the acquired image data is processed to recognize an operational authority of the operator based on the recognition processing.

34. A method of controlling an object, the method comprising steps of:
- acquiring a predetermined number of image data of an operator in a predetermined time period;
- performing recognition processing on the acquired image data;
- defining a virtual plane in between the object and the operator;
- determining if a predetermined part of the operator penetrates the virtual plane based on the recognition processing when the predetermined part of operator penetrates the first virtual plane for more than a variable predetermined period; and
- controlling the object based on the determination.

* * * * *